United States Patent
Roscow

(10) Patent No.: US 11,466,283 B2
(45) Date of Patent: Oct. 11, 2022

(54) PLANTS AND METHODS FOR INCREASING AND DECREASING SYNTHESIS OF CANNABINOIDS

(71) Applicant: Canopy Growth Corporation, Smith Falls (CA)

(72) Inventor: Robert F. Roscow, Boulder, CO (US)

(73) Assignee: Canopy Growth Corporation, Smith Falls (CA)

( * ) Notice: Subject to any disclaimer, the term of this patent is extended or adjusted under 35 U.S.C. 154(b) by 46 days.

(21) Appl. No.: 16/326,664

(22) PCT Filed: Aug. 18, 2017

(86) PCT No.: PCT/US2017/047587
§ 371 (c)(1),
(2) Date: Feb. 19, 2019

(87) PCT Pub. No.: WO2018/035450
PCT Pub. Date: Feb. 22, 2018

(65) Prior Publication Data
US 2020/0181631 A1 Jun. 11, 2020

Related U.S. Application Data

(60) Provisional application No. 62/376,521, filed on Aug. 18, 2016, provisional application No. 62/385,102, filed on Sep. 8, 2016, provisional application No. 62/416,084, filed on Nov. 1, 2016, provisional application No. 62/416,098, filed on Nov. 1, 2016, provisional application No. 62/429,039, filed on Dec. 1, 2016, provisional application No. 62/429,046, filed on Dec. 1, 2016, provisional application No. 62/429,049, filed on Dec. 1, 2016.

(51) Int. Cl.
*C12N 15/82* (2006.01)
*A01H 6/28* (2018.01)

(52) U.S. Cl.
CPC ..... *C12N 15/8243* (2013.01); *C12N 15/8213* (2013.01)

(58) Field of Classification Search
None
See application file for complete search history.

(56) References Cited

U.S. PATENT DOCUMENTS

| | | | |
|---|---|---|---|
| 9,611,460 B2* | 4/2017 | Page | C12N 15/70 |
| 2013/0067619 A1 | 3/2013 | Page et al. | |
| 2014/0245494 A1 | 8/2014 | Cohen | |
| 2014/0298511 A1 | 10/2014 | Lewis et al. | |
| 2015/0128301 A1 | 5/2015 | Page et al. | |
| 2016/0177404 A1 | 6/2016 | McKernan | |
| 2018/0258439 A1* | 9/2018 | Boudko | A61K 31/352 |

FOREIGN PATENT DOCUMENTS

| | | |
|---|---|---|
| WO | WO 2016/033246 A1 | 3/2016 |
| WO | WO 2016/189384 A1 | 12/2016 |

OTHER PUBLICATIONS

Sirikantaramas et al, *Cannabis sativa* L.—Botany and Biotechnology, 2017, section 8, 183-206.*
Morimoto et al, 2007, The Journal of Biological Chemistry, 282:20739-20751.*
Coogan et al, 2019, Journal of Cannabis Research, 1:1-11.*
Fournier et al, 1987, Plant medica, 277-279.*
Pacifico et al, 2006, Molecular Breeding, 17:257-268.*
Supplementary European Search Report regarding Europe Patent Application No. 17842206 dated Nov. 29, 2019.
MacKinnon, et al., "Progress towards transformation of fibre hemp", Scottish Crop Research Institute Annual Report;Jan. 1, 2001; pp. 84-86; Retrieved from the Internet: URL:https://www.google.nl/url?sa=t&rct=j&q=&esrc=s&source=web&cd=1&ved=0ahUKEwiu_42Fs63RAhXH7hoKHQ51DNQQFgghMAA&url=http://www.scri.ac.uk/scri/file/annualreports/2001/11HEMP.PDF&usg=AFQjCNFTXPr4LZw9gcIHOMOs_IMjsQHj6A[retrieved on Jan. 6, 2017].
Waby, et al., "Agrobacterium infection of hemp (*Cannabis sativa* L.): establishment of hairy root cultures", Journal of Plant Interactions,8(4):312-320, 2013.
Bortesi et al., "The CRISPR/Cas9 system for plant genome-editing and beyond", Biotechnology Advances, 33(1):41-52, 2015.
International Preliminary Report on Patentability regarding International Application No. PCT/US2017/047587, dated Feb. 19, 2019.
International Search Report and Written Opinion regarding International Application No. PCT/US2017/047587, dated Nov. 17, 2017.
Van Bakel, et al., "The Draft Genome and Transcriptome of Cannabis Sativa," Genome Biology 12(10):1-18 (2011).

* cited by examiner

Primary Examiner — Jason Deveau Rosen
(74) Attorney, Agent, or Firm — Dentons US LLP

(57) ABSTRACT

This disclosure relates to new plants and methods for increasing and decreasing synthesis of cannabinoids. The plants disclosed herein comprise unnatural ratios and concentrations of cannabinoids in plants of genus *Cannabis*. The methods disclosed herein comprise manipulating the biosynthetic pathway of cannabinoids to produce plants of genus *Cannabis* with unnatural ratios and concentrations of cannabinoids.

4 Claims, No Drawings
Specification includes a Sequence Listing.

SEQUENCE LISTING

```
<160> NUMBER OF SEQ ID NOS: 6

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gccggagcta cccttggaga agtttattat tggg                                 34

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gagctaccct tggagaagtt tattattggg                                      30

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ccggagctac ccttggagaa gtt                                             23

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
aacttctcca agggtagctc cgg                                             23

<210> SEQ ID NO 5
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
aacttctcca agggtagctc                                                    20

<210> SEQ ID NO 6
<211> LENGTH: 573
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
cacaattcca cacaacatac gagcccttt  tttcttcttc ttcgttcata cagttttttt        60
ttgtttatca gcttacattt tcttgaaccg tagctttcgt tttcttcttt ttaactttcc       120
attcggagtt tttgtatctt gtttcatagt ttgtcccagg attagaatga ttaggcatcg       180
aaccttcaag aatttgattg aataaaacat cttcattctt aagatatgaa gataatcttc       240
aaaaggcccc tgggaatctg aaagaagaga agcaggccca tttatatggg aaagaacaat       300
agtatttctt atataggccc atttaagttg aaaacaatct tcaaaagtcc cacatcgctt       360
agataagaaa acgaagctga gtttatatac agctagagtc gaagtagtga ttgaacttct       420
ccaagggtag ctcgttttag agctagaaat agcaagttaa aataaggcta gtccgttatc       480
aacttgaaaa agtggcaccg agtcggtgct ttttttctag acccagcttt cttgtacaaa       540
gttggcatta agcggagaat taagggagtc acg                                   573
```

PLANTS AND METHODS FOR INCREASING AND DECREASING SYNTHESIS OF CANNABINOIDS

CROSS-REFERENCE TO OTHER RELATED APPLICATIONS

This application is a 371 National Stage application of International Application No. PCT/US2017/047587, filed Aug. 18, 2017, which claims priority to U.S. Provisional Application Ser. No. 62/376,521 filed on Aug. 18, 2016, U.S. Provisional Application Ser. No. 62/385,102 filed on Sep. 8, 2016, U.S. Provisional Application Ser. No. 62/416,084 filed on Nov. 1, 2016, U.S. Provisional Application Ser. No. 62/416,098 filed on Nov. 1, 2016, U.S. Provisional Application Ser. No. 62/429,039 filed on Dec. 1, 2016, U.S. Provisional Application Ser. No. 62/429,046 filed on Dec. 1, 2016, and U.S. Provisional Application Ser. No. 62/429,049 filed on Dec. 1, 2016, each of which is hereby incorporated by reference in their entirety.

SEQUENCE LISTING

The instant application contains a Sequence Listing which has been submitted electronically in ASCII format and is hereby incorporated by reference in its entirety. Said ASCII copy, created on Sep. 22, 2017, is named 10064-0012-304_SL.txt and is 2,644 bytes in size.

TECHNICAL FIELD

This disclosure relates to the *cannabis* industry. In particular, this disclosure relates to new, manmade plants of genus *Cannabis*.

BACKGROUND

The word "*cannabis*" refers to a genus of flowering plants. Plants of genus *Cannabis* include several species, including *Cannabis sativa, Cannabis indica,* and *Cannabis ruderalis*. There is a long history of cultivating plants of genus *Cannabis* for hemp fibers, seeds and seed oils, medicinal purposes, and recreational activities.

According to some accounts, *cannabis* is composed of at least 483 known chemical compounds, which include cannabinoids, terpenoids, flavonoids, nitrogenous compounds, amino acids, proteins, glycoproteins, enzymes, sugars and related compounds, hydrocarbons, alcohols, aldehydes, ketones, acids, fatty acids, esters, lactones, steroids, terpenes, non-cannabinoid phenols, vitamins, and pigments.

Cannabinoids are of particular interest for research and commercialization. Usually, cannabinoids are extracted from the *cannabis* plant as part of a crude mixture, combined with other chemical compounds found in the *cannabis* plant. Most extractions of *cannabis* plant matter aim to extract cannabinoids, particularly tetrahydrocannabinol (THC). THC is useful for relieving pain, treating glaucoma, and relieving nausea. THC is also gaining immense popularity as a recreational drug substance. Other cannabinoids of interest include, Cannabigerol (CBG), Cannabigerolic Acid (CBGA), Cannabidiol (CBD), Cannabinol (CBN), Cannabichromene (CBC), Tetrahydrocannabivarin (THCV), Cannabigerovarin (CBGV), and Cannabigerovarinic Acid (CBGVA).

A variety of growing and cultivating techniques have been developed for increasing the production of secondary compounds within plants of genus *Cannabis*. These techniques include outdoor cultivation, indoor cultivation, hydroponics, fertilization, atmospheric manipulation, cloning, crossbreeding, Screen of Grow (SCROG), Sea of Green (SOG), pinching, training, topping, etc.

While breeding and farming techniques yield plants with high concentrations of cannabinoids, these techniques fail to provide the level of control and production needed. Cannabinoid research is still new and having plants producing certain cannabinoids would be advantageous for research and development. Furthermore, separating hundreds of molecules can prove challenging and time consuming, even for experienced chemists.

There exists a need for a plant of the genus *Cannabis* producing particular amounts of cannabinoids—higher in some cases and lower in others. In particular, plants of genus *Cannabis* selectively producing certain cannabinoids over others. There also exists a need for plants of genus *Cannabis* producing unnaturally occurring ratios and/or concentrations of cannabinoids. There also exists a need for manipulating the biosynthetic pathways of a plant of genus *Cannabis*.

DETAILED DESCRIPTION

Disclosed herein are new plants of genus *Cannabis*. In one embodiment, the plant of genus *Cannabis* produces unnaturally occurring ratios and/or concentrations of cannabinoids. In one embodiment, the plant of genus *Cannabis* preferentially produces a first cannabinoid in a higher quantity than a second cannabinoid. In one embodiment, the plant of genus *Cannabis* preferentially produces a first cannabinoid in a lower quantity than a second cannabinoid. In one embodiment, the plant of genus *Cannabis* is manmade.

Disclosed herein is a new method of producing a plant of genus *Cannabis*. In one embodiment, the method disclosed herein comprises controlling the biosynthetic pathway of one or more cannabinoids. In one embodiment, the method disclosed herein comprises manipulating the expression of one or more cannabinoid synthesis enzymes.

Disclosed herein is a new plant of genus *Cannabis*, comprising:
 a total cannabinoid content;
 a first cannabinoid comprising greater than 10% of the total cannabinoid content by dry weight;
 a second cannabinoid comprising less than 10% of the total cannabinoid content by dry weight; and
 modified genetic material within a genome of the plant of genus *Cannabis*.

In one embodiment, the first cannabinoid is chosen from Cannabigerolic Acid (CBGA), Cannabigerolic Acid monomethylether (CBGAM), Cannabigerol (CBG), Cannabigerol monomethylether (CBGM), Cannabigerovarinic Acid (CBGVA), Cannabigerovarin (CBGV), Cannabichromenic Acid (CBCA), Cannabichromene (CBC), Cannabichromevarinic Acid (CBCVA), Cannabichromevarin (CBCV), Cannabidiolic Acid (CBDA), Cannabidiol (CBD), Cannabidiol monomethylether (CBDM), Cannabidiol-$C_4$ (CBD-$C_4$), Cannabidivarinic Acid (CBDVA), Cannabidivarin (CBDV), Cannabidiorcol (CBD-$C_1$), Tetrahydrocannabinolic acid A (THCA-A), Tetrahydrocannabinolic acid B (THCA-B), Tetrahydrocannabinolic Acid (THCA), Tetrahydrocannabinol (THC), Tetrahydrocannabinolic acid $C_4$ (THCA-$C_4$), Tetrahydrocannbinol $C_4$ (THC-$C_4$), Tetrahydrocannabivarinic acid (THCVA), Tetrahydrocannabivarin (THCV), Tetrahydrocannabiorcolic acid (THCA-$C_1$), Tetrahydrocannabiorcol (THC-$C_1$), $\Delta^7$-cis-iso-tetrahydrocannabivarin, $\Delta^8$-tetrahydrocannabinolic acid ($\Delta$8-THCA), Cannabivarinodiolic (CBNDVA), Cannabivarinodiol (CBNDV), Δ⁸-tetrahydrocannabinol (Δ⁸-THC), Δ⁹-tetrahydrocannabinol (Δ⁹-THC), Cannabicyclolic acid (CBLA), Cannabicyclol (CBL), Cannabicyclovarin (CBLV), Cannabielsoic acid A (CBEA-A), Cannabielsoic acid B (CBEA-B), Cannabielsoin (CBE), Cannabivarinselsoin (CBEV), Cannabivarinselsoinic Acid (CBEVA), Cannabielsoic Acid (CBEA), Cannabielvarinsoin (CBLV), Cannabielvarinsoinic Acid (CBLVA), Cannabinolic acid (CBNA), Cannabinol (CBN), Cannabivarinic Acid (CBNVA), Cannabinol methylether (CBNM), Cannabinol-C₄ (CBN-C₄), Cannabivarin (CBV), Cannabino-C₂(CBN-C₂), Cannabiorcol (CBN-C₁), Cannabinodiol (CBND), Cannabinodiolic Acid (CBNDA), Cannabinodivarin (CBDV), Cannabitriol (CBT), 10-Ethoxy-9-hydroxy-Δ$^{6a}$-tetrahydrocannabinol, 8,9-Dihydroxy-Δ$^{6a(10a)}$-tetrahydrocannabinol (8,9-Di-OH-CBT-C₅), Cannabitriolvarin (CBTV), Ethoxy-cannabitriolvarin (CBTVE), Dehydrocannabifuran (DCBF), Cannbifuran (CBF), Cannabichromanon (CBCN), Cannabicitran (CBT), 10-Oxo-Δ$^{6a(10a)}$-tetrahydrocannabinol (OTHC), Δ⁹-cis-tetrahydrocannabinol (cis-THC), Cannabiripsol (CBR), 3,4,5,6-tetrahydro-7-hydroxy-alpha-alpha-2-trimethyl-9-n-propyl-2,6-methano-2H-1-benzoxocin-5-methanol (OH-iso-HHCV), Trihydroxy-delta-9-tetrahydrocannabinol (triOH-THC), Yangonin, Epigallocatechin gallate, Dodeca-2E, 4E, 8Z, 10Z-tetraenoic acid isobutylamide, and Dodeca-2E,4E-dienoic acid isobutylamide.

In one embodiment, the second cannabinoid is chosen from Cannabigerolic Acid (CBGA), Cannabigerolic Acid monomethylether (CBGAM), Cannabigerol (CBG), Cannabigerol monomethylether (CBGM), Cannabigerovarinic Acid (CBGVA), Cannabigerovarin (CBGV), Cannabichromenic Acid (CBCA), Cannabichromene (CBC), Cannabichromevarinic Acid (CBCVA), Cannabichromevarin (CBCV), Cannabidiolic Acid (CBDA), Cannabidiol (CBD), Cannabidiol monomethylether (CBDM), Cannabidiol-C₄ (CBD-C₄), Cannabidivarinic Acid (CBDVA), Cannabidivarin (CBDV), Cannabidiorcol (CBD-C₁), Tetrahydrocannabinolic acid A (THCA-A), Tetrahydrocannabinolic acid B (THCA-B), Tetrahydrocannabinolic Acid (THCA), Tetrahydrocannabinol (THC), Tetrahydrocannabinolic acid C₄ (THCA-C₄), Tetrahydrocannbinol C₄ (THC-C₄), Tetrahydrocannabivarinic acid (THCVA), Tetrahydrocannabivarin (THCV), Tetrahydrocannabiorcolic acid (THCA-C₁), Tetrahydrocannabiorcol (THC-C₁), Δ⁷-cis-iso-tetrahydrocannabivarin, Δ⁸-tetrahydrocannabinolic acid (Δ8-THCA), Cannabivarinodiolic (CBNDVA), Cannabivarinodiol (CBNDV), Δ⁸-tetrahydrocannabinol (Δ⁸-THC), Δ⁹-tetrahydrocannabinol (Δ⁹-THC), Cannabicyclolic acid (CBLA), Cannabicyclol (CBL), Cannabicyclovarin (CBLV), Cannabielsoic acid A (CBEA-A), Cannabielsoic acid B (CBEA-B), Cannabielsoin (CBE), Cannabivarinselsoin (CBEV), Cannabivarinselsoinic Acid (CBEVA), Cannabielsoic Acid (CBEA), Cannabielvarinsoin (CBLV), Cannabielvarinsoinic Acid (CBLVA), Cannabinolic acid (CBNA), Cannabinol (CBN), Cannabivarinic Acid (CBNVA), Cannabinol methylether (CBNM), Cannabinol-C₄ (CBN-C₄), Cannabivarin (CBV), Cannabino-C₂(CBN-C₂), Cannabiorcol (CBN-C₁), Cannabinodiol (CBND), Cannabinodiolic Acid (CBNDA), Cannabinodivarin (CBDV), Cannabitriol (CBT), 10-Ethoxy-9-hydroxy-Δ$^{6a}$-tetrahydrocannabinol, 8,9-Dihydroxy-Δ$^{6a(10a)}$-tetrahydracannabinol (8,9-Di-OH-CBT-C₅), Cannabitriolvarin (CBTV), Ethoxy-cannabitriolvarin (CBTVE), Dehydrocannabifuran (DCBF), Cannbifuran (CBF), Cannabichromanon (CBCN), Cannabicitran (CBT), 10-Oxo-Δ$^{6a(10a)}$-tetrahydrocannabinol (OTHC), Δ⁹-cis-tetrahydrocannabinol (cis-THC), Cannabiripsol (CBR), 3,4,5,6-tetrahydro-7-hydroxy-alpha-alpha-2-trimethyl-9-n-propyl-2,6-methano-2H-1-benzoxocin-5-methanol (OH-iso-HHCV), Trihydroxy-delta-9-tetrahydrocannabinol (triOH-THC), Yangonin, Epigallocatechin gallate, Dodeca-2E, 4E, 8Z, 10Z-tetraenoic acid isobutylamide, and Dodeca-2E,4E-dienoic acid isobutylamide.

In one embodiment, the first cannabinoid is chosen from THC, D9-THC, D8-THC, THCA, THCV, D8-THCV, D9-THCV, THCVA, CBD, CBDA, CBDV, CBDVA, CBC, CBCA, CBCV, CBCVA, CBG, CBGA, CBGV, CBGVA, CBN, CBNA, CBNV, CBNVA, CBND, CBNDA, CBNDV, CBNDVA, CBE, CBEA, CBEV, CBEVA, CBL, CBLA, CBLV, or CBLVA.

In one embodiment, the second cannabinoid is chosen from THC, D9-THC, D8-THC, THCA, THCV, D8-THCV, D9-THCV, THCVA, CBD, CBDA, CBDV, CBDVA, CBC, CBCA, CBCV, CBCVA, CBG, CBGA, CBGV, CBGVA, CBN, CBNA, CBNV, CBNVA, CBND, CBNDA, CBNDV, CBNDVA, CBE, CBEA, CBEV, CBEVA, CBL, CBLA, CBLV, or CBLVA.

In one embodiment, the plant of genus *Cannabis* comprises producing CBC in an unnaturally occurring ratio with respect to the total cannabinoid content. In one embodiment, the plant of genus *Cannabis* comprises an unnaturally occurring concentration of CBC.

In one embodiment, the plant of genus *Cannabis* comprises producing CBD in an unnaturally occurring ratio with respect to the total cannabinoid content. In one embodiment, the plant of genus *Cannabis* comprises an unnaturally occurring concentration of CBD.

In one embodiment, the plant of genus *Cannabis* comprises producing CBG in an unnaturally occurring ratio with respect to the total cannabinoid content. In one embodiment, the plant of genus *Cannabis* comprises an unnaturally occurring concentration of CBG.

In one embodiment, the plant of genus *Cannabis* comprises producing CBCA in an unnaturally occurring ratio with respect to the total cannabinoid content. In one embodiment, the plant of genus *Cannabis* comprises an unnaturally occurring concentration of CBCA.

In one embodiment, the plant of genus *Cannabis* comprises producing CBDA in an unnaturally occurring ratio with respect to the total cannabinoid content. In one embodiment, the plant of genus *Cannabis* comprises an unnaturally occurring concentration of CBDA.

In one embodiment, the plant of genus *Cannabis* comprises producing CBGA in an unnaturally occurring ratio with respect to the total cannabinoid content. In one embodiment, the plant of genus *Cannabis* comprises an unnaturally occurring concentration of CBGA.

In one embodiment, the plant of genus *Cannabis* comprises producing THCA in an unnaturally occurring ratio with respect to the total cannabinoid content. In one embodiment, the plant of genus *Cannabis* comprises an unnaturally occurring concentration of THCA.

In one embodiment, the plant of genus *Cannabis* comprises producing THCV in an unnaturally occurring ratio with respect to the total cannabinoid content. In one embodiment, the plant of genus *Cannabis* comprises an unnaturally occurring concentration of THCV.

In one embodiment, the plant of genus *Cannabis* comprises producing CBCV in an unnaturally occurring ratio with respect to the total cannabinoid content. In one embodiment, the plant of genus *Cannabis* comprises an unnaturally occurring concentration of CBCV.

In one embodiment, the plant of genus *Cannabis* comprises producing CBDV in an unnaturally occurring ratio with respect to the total cannabinoid content. In one embodiment, the plant of genus *Cannabis* comprises an unnaturally occurring concentration of CBDV.

In one embodiment, the plant of genus *Cannabis* comprises producing CBGV in an unnaturally occurring ratio with respect to the total cannabinoid content. In one embodiment, the plant of genus *Cannabis* comprises an unnaturally occurring concentration of CBGV.

In one embodiment, the plant of genus *Cannabis* comprises producing THCVA in an unnaturally occurring ratio with respect to the total cannabinoid content. In one embodiment, the plant of genus *Cannabis* comprises an unnaturally occurring concentration of THCVA.

In one embodiment, the plant of genus *Cannabis* comprises producing CBCVA in an unnaturally occurring ratio with respect to the total cannabinoid content. In one embodiment, the plant of genus *Cannabis* comprises an unnaturally occurring concentration of CBCVA.

In one embodiment, the plant of genus *Cannabis* comprises producing CBDVA in an unnaturally occurring ratio with respect to the total cannabinoid content. In one embodiment, the plant of genus *Cannabis* comprises an unnaturally occurring concentration of CBDVA.

In one embodiment, the plant of genus *Cannabis* comprises producing CBGVA in an unnaturally occurring ratio with respect to the total cannabinoid content. In one embodiment, the plant of genus *Cannabis* comprises an unnaturally occurring concentration of CBGVA.

As used herein, the term "cannabinoid" refers to a compound belonging to a class of secondary compounds commonly found in plants of genus *Cannabis*. In one embodiment, the cannabinoid is found in a plant, e.g., a plant of genus *Cannabis*. In one embodiment, the cannabinoid is referred to as a phytocannabinoid. In one embodiment, the cannabinoid is found in a mammal. In one embodiment, the cannabinoid is referred to as a endocannabinoid. In one embodiment, the cannabinoid is made in a laboratory setting. In one embodiment, the cannabinoid is referred to as a synthetic cannabinoid. In one embodiment, the cannabinoid acts upon a cellular receptor, such as a G-coupled protein receptor (e.g., a serotonin receptor, a cannabinoid receptor, TRPV1, an opioid receptor, etc.) thereby causing a response on the brain or body. In one embodiment, the cannabinoid affects the activity of other compounds at one or more receptors by acting as an agonist, partial agonist, inverse agonist, antagonist, etc.

In many cases, a cannabinoid can be identified because its chemical name will include the text string "*cannabi*" in the name.

Within the context of this disclosure, where reference is made to a particular cannabinoid, each of the acid and/or decarboxylated forms are contemplated as both single molecules and mixtures of the acid and/or decarboxylated forms.

As used herein, the term "secondary compound" refers to a non-vital compound required for an organism's survival. In one embodiment, the secondary compound is not directly involved in the growth of an organism. In one embodiment, the secondary compound is not directly involved in the development of an organism. In one embodiment, the secondary compound is not directly involved in the reproduction of an organism. In one embodiment, the secondary compound is a cannabinoid. In one embodiment, the secondary compound is a terpene.

As used herein, the term "total cannabinoid content" refers to the entire amount of identifiable cannabinoids within a sample, e.g., a plant, a plant part, a crude extract from a plant, etc. In one embodiment, the total cannabinoid content is the total amount of cannabinoids within a plant of genus *Cannabis*. In one embodiment, the total cannabinoid content is the total amount of cannabinoids within a trichome from a plant of genus *Cannabis*. In one embodiment, the total cannabinoid content is expressed in mass, e.g., grams. In one embodiment, the total cannabinoid content is expressed in moles. In one embodiment, the total cannabinoid content is expressed in molecular weight. In one embodiment, the total cannabinoid content is expressed by dry weight.

As used within the context of this application, the term "manmade" means engineered or purposefully created by a human in contrast to naturally occurring "in nature" without human influence. In one embodiment, manmade plants are plant made by manipulating the genetic code of a plant to express one or more characteristics in an unnaturally occurring way.

As used herein, the term "naturally occurring" refers to materializing, arising, happening, or synthesizing in nature. In one embodiment, naturally occurring refers to a secondary compound synthesized within a plant. In one embodiment, naturally occurring refers to a collection of cannabinoids synthesized within a plant of genus *Cannabis*. In one embodiment, naturally occurring refers to the concentrations of compounds within a plant. In one embodiment, naturally occurring refers to the concentration of cannabinoids within a plant of genus *Cannabis*. In one embodiment, naturally occurring refers to the ratio of a secondary compound to all secondary compounds within a plant. In one embodiment, naturally occurring refers to the ratio of a first cannabinoid with respect to the total cannabinoid content within a plant of genus *Cannabis*.

As used herein, the term "naturally occurring ratio" refers to the proportion of one compound or compounds in relation to another compound or compounds within a naturally occurring plant of genus *Cannabis*. In one embodiment, the naturally occurring ratio is the amount of a first cannabinoid in relation to the total cannabinoid content within a plant of genus *Cannabis*. In one embodiment, the naturally occurring ratio is expressed as a molar ratio. In one embodiment, the naturally occurring ratio is expressed as a mass ratio. In one embodiment, the mass and/or molar ratio is measured by chromatography and/or spectroscopy, e.g., HPLC, GC, and/or mass spectroscopy. In one embodiment, the naturally occurring ratio is expressed as a dry weight.

As used herein, the term "unnaturally occurring ratio" refers to the proportion of one compound or compounds in relation to another compound or compounds in a composition, e.g., a plant, a plant derived substance such as a crude extract, created by a human. In one embodiment, the unnaturally occurring ratio is the amount of a first cannabinoid in relation to total cannabinoid content and is not observed in a naturally occurring plant of genus *Cannabis*. In one embodiment, the unnaturally occurring ratio is expressed as a molar ratio. In one embodiment, the unnaturally occurring ratio is expressed in dry weight ratio. In one embodiment, the unnaturally occurring ratio is expressed as a mass ratio. In one embodiment, the mass and/or molar ratio is measured by chromatography and/or spectroscopy, e.g., HPLC, GC, and/or mass spectroscopy. In one embodiment, the unnaturally occurring ratio occurs as a result of genetic modification of a plant of genus *Cannabis*. In one embodiment, the unnaturally occurring ratio comprises an unnaturally occurring concentration of a first cannabinoid comprises and a naturally occurring concentration of the total cannabinoid content. In one embodiment, the unnaturally occurring ratio comprises a naturally occurring ratio of a first cannabinoid and an unnaturally occurring concentration of the total cannabinoid content. In one embodiment, the unnaturally occurring ratio comprises a unnaturally occurring ratio of a first cannabinoid and an unnaturally occurring concentration of the total cannabinoid content.

As used herein, the term "naturally occurring concentration" refers to the amount, e.g., percent mass, mass, moles, etc., of a compound or compounds in relation to an entire naturally occurring reference sample. For example, the percentage of THC within a plant of genus *Cannabis* that has not been modified as described in this disclosure. In one embodiment, the naturally occurring concentration is the percent mass of a cannabinoid in a sample of a plant of genus *Cannabis*. In one embodiment, the naturally occurring concentration is the mass of a cannabinoid within the dried, or cured, flower of a plant of genus *Cannabis*. In one embodiment, the naturally occurring concentration is the dry weight of a first cannabinoid within a crude extract of a plant of genus *Cannabis*.

As used herein, the term "unnaturally occurring concentration" refers to the amount, e.g., percent mass, mass, moles, etc., of a compound or compounds in relation to an entire sample within a manmade composition. For example, the percentage of THC within a plant of genus *Cannabis* modified as described in this disclosure. In one embodiment, the unnaturally occurring concentration is the molecular weight of a first cannabinoid in relation to the total cannabinoid content. In one embodiment, the unnaturally occurring concentration is measured by moles and expressed as Molarity. In one embodiment, the unnaturally occurring concentration is measured by percent mass. In one embodiment, the unnaturally occurring concentration is measured by dry weight. In one embodiment, the unnaturally occurring concentration occurs as a result of genetic modification of a plant of genus *Cannabis*.

In one embodiment, the plant of genus *Cannabis* comprises the first cannabinoid comprises 10-50% of the total cannabinoid content by dry weight and the second cannabinoid comprises 0-10% by dry weight of the total cannabinoid content.

In one embodiment, the plant of genus *Cannabis* comprises the first cannabinoid comprises 15-45% of the total cannabinoid content by dry weight and the second cannabinoid comprises 0.5-7.5% by dry weight of the total cannabinoid content.

In one embodiment, the plant of genus *Cannabis* comprises the first cannabinoid comprises 20-40% of the total cannabinoid content by dry weight and the second cannabinoid comprises 1-5% by dry weight of the total cannabinoid content.

In one embodiment, the plant of genus *Cannabis* comprises the first cannabinoid comprises 25-35% of the total cannabinoid content by dry weight and the second cannabinoid comprises 1.5-2.5% by dry weight of the total cannabinoid content.

In one embodiment, the plant of genus *Cannabis* comprises a third cannabinoid. In one embodiment, the plant of genus *Cannabis* comprises a fourth cannabinoid. In one embodiment, the plant of genus *Cannabis* comprises more than four cannabinoids.

As used herein, the term "total mass" refers to the entire amount of matter for a given reference sample. In one embodiment, the total mass is measured by molecular mass. In one embodiment, the total mass is measured by mass, e.g., grams. In one embodiment, the total mass is the dry weight of a plant of genus *Cannabis*. In one embodiment, the total mass is the dry weight of a crude extract from a plant of genus *Cannabis*. In one embodiment, the total mass is the dry weight of a purified extract from a plant of genus *Cannabis* after removing all the water.

Disclosed herein are new methods of producing a plant of genus *Cannabis* comprising comparing the genetic sequence of two plants, correlating the sequence differences with a phenotype of interest, and modifying the genome of a plant to bolster the expression of the desired phenotype. In one embodiment, the methods disclosed herein comprise overexpressing a gene sequence. In one embodiment, the methods disclosed herein comprise underexpressing a gene sequence. In one embodiment, the methods disclosed herein comprise manipulating the biosynthetic pathway of cannabinoids.

Disclosed herein are new plants of genus *Cannabis* comprising modified genetic material, wherein the modified genetic material affects enzymes associated with producing secondary compounds. In one embodiment, the modified genetic material codes for CBCA synthase. In one embodiment, the modified genetic material codes for CBDA synthase. In one embodiment, the modified genetic material codes for THCA synthase. In one embodiment, the modified genetic material codes for olivetolic acid cyclase. In one embodiment, the modified genetic material codes for tetraketide synthase. In one embodiment, the modified genetic material codes for aromatic prenyltransferase.

Disclosed herein is a new method of regulating cannabinoid biosynthesis within a plant of genus *Cannabis* by destroying enzymes facilitating cannabinoid synthesis. In one embodiment, destroying comprises mutating a gene. In one embodiment, destroying comprises interfering with gene expression. In one embodiment, destroying comprises cleaving genes within a genome.

As used herein, the term "destroying" means inhibiting an enzyme and/or compound involved in the biosynthesis of a cannabinoid. In one embodiment, destroying comprises inhibiting the expression of an enzyme. In one embodiment, destroying comprises increasing the production of promoters.

As used herein, the term "plant" means a multicellular eukaryote of the kingdom Plantae, whether naturally occurring, completely man-made, or some combination thereof. In one embodiment, the plant is from the genus *Cannabis*. In one embodiment, the plant is a part of a plant, e.g., a leaf, a root, a stem, etc. In one embodiment, the plant is dried, e.g., dehydrated in an oven.

As used herein, the term "genus *Cannabis*" refers to an organism belonging to the genus *Cannabis* within the biological taxonomical system. In one embodiment, genus *Cannabis* comprises the species *Cannabis sativa*. In one embodiment, genus *Cannabis* comprises the species *Cannabis indica*. In one embodiment, genus *Cannabis* comprises the species *Cannabis ruderalis*. In one embodiment, genus *Cannabis* comprises various strains.

As used herein, the term "flower" within the context of this disclosure refers to a reproductive structure of a plant of genus *Cannabis*, which includes male, female, and/or hermaphroditic plants. The term "flower" also encompasses any part or compound involved in or created during the flowering process.

In one embodiment, the term flower includes a bud produced at the end of the flowering stage. In one embodiment, the term flower includes a trichome, which produce secondary compounds, e.g., cannabinoids, terpenes, etc. In one embodiment, the term flower includes plant material sold commercially for recreational and/or medical use or processing.

As used herein, the term "THC" refers to tetrahydrocannabinol and has the following structural formula:

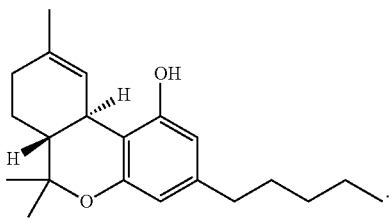 [SMILES: CCCCCc1cc(O)c2c(c1)OC(C)(C)[C@@H]1CCC(C)=C[C@@H]21]

Within the context of this disclosure, plants of genus *Cannabis* are modified to produce THC in controlled levels.

As used herein, the term "THCA" refers to tetrahydrocannabinolic acid and has the following structural formula:

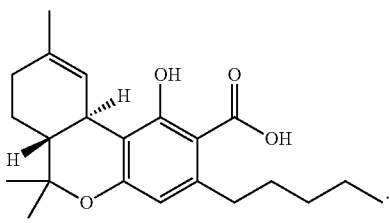 [SMILES: CCCCCc1cc2c(c(O)c1C(=O)O)[C@@H]1C=C(C)CC[C@H]1C(C)(C)O2]

Decarboxylating THCA with heat, light, etc., forms THC, D8-THC, D9-THC, and other potential cannabinoids. Within the context of this disclosure, plants of genus *Cannabis* are modified to produce THCA in controlled levels.

As used herein, the term "THCV" refers to tetrahydrocannabivarin and has the following structural formula:

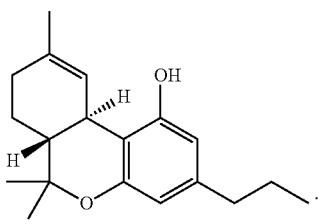 [SMILES: CCCc1cc(O)c2c(c1)OC(C)(C)[C@@H]1CCC(C)=C[C@@H]21]

Within the context of this disclosure, plants of genus *Cannabis* are modified to produce THCV in controlled levels.

As used herein, the term "THCVA" refers to tetrahydrocannabivarinic acid and has the following structural formula:

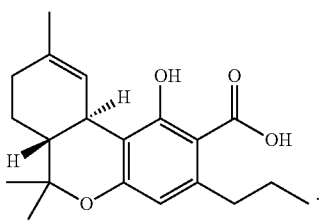 [SMILES: CCCc1cc2c(c(O)c1C(=O)O)[C@@H]1C=C(C)CC[C@H]1C(C)(C)O2]

Decarboxylating THCVA with heat, light, etc., forms THCV, D8-THCV, D9-THCV, and other possible cannabinoid derivatives. Within the context of this disclosure, plants of genus *Cannabis* are modified to produce THCVA in controlled levels.

As used herein, the term "D8-THC" refers to delta-8-tetrahydrocannabinol and has the following structural formula:

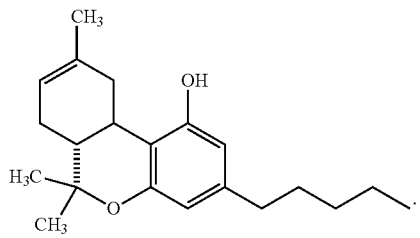

Within the context of this disclosure, plants of genus *Cannabis* are modified to produce D8-THC in controlled levels.

As used herein, the term "D8-THCV" refers to delta-8-tetrahydrocannabivarin and has the following structural formula:

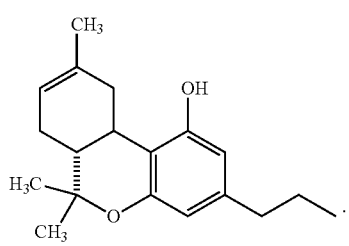

Within the context of this disclosure, plants of genus *Cannabis* are modified to produce D8-THCV in controlled levels.

As used herein, the term "D9-THC" refers to delta-9-tetrahydrocannabinol and has the following structural formula:

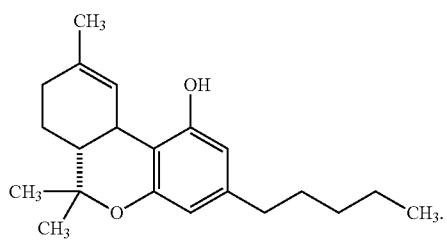

Within the context of this disclosure, plants of genus *Cannabis* are modified to produce D9-THC in controlled levels.

As used herein, the term "D9-THCV" refers to delta-9-tetrahydrocannabivarin and has the following structural formula:

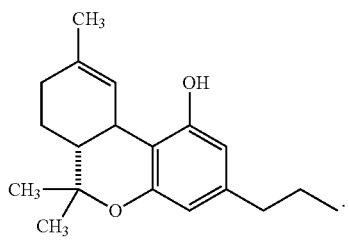

Within the context of this disclosure, plants of genus *Cannabis* are modified to produce D9-THCV in controlled levels.

As used herein, the term "CBD" refers to cannabidiol and has the following structural formula:

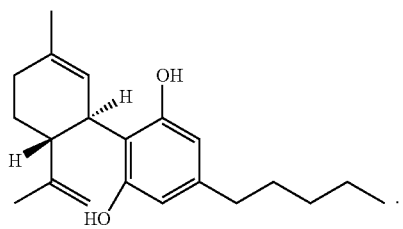 [SMILES: C=C(C)[C@@H]1CCC(C)=C[C@H]1c1c(O)cc(CCCCC)cc1O]

Within the context of this disclosure, plants of genus *Cannabis* are modified to produce CBD in controlled levels.

As used herein, the term "CBDA" refers to cannabidiolic acid and has the following structural formula:

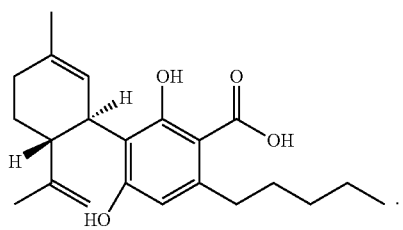 [SMILES: C=C(C)[C@@H]1CCC(C)=C[C@H]1c1c(O)cc(CCCCC)c(C(=O)O)c1O]

Decarboxylating CBDA with heat, light, etc., forms CBD and other possible cannabinoid derivatives. Within the context of this disclosure, plants of genus *Cannabis* are modified to produce CBDA in controlled levels.

As used herein, the term "CBDV" refers to cannabidivarin and has the following structural formula:

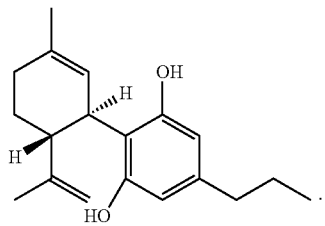 [SMILES: C=C(C)[C@@H]1CCC(C)=C[C@H]1c1c(O)cc(CCC)cc1O]

Within the context of this disclosure, plants of genus *Cannabis* are modified to produce CBDV in controlled levels.

As used herein, the term "CBDVA" refers to cannabidivarinic acid and has the following structural formula:

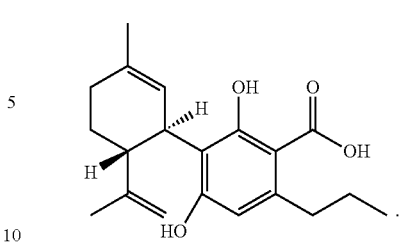

Decarboxylating CBDVA with heat, light, etc., forms CBDV and other possible cannabinoid derivatives. Within the context of this disclosure, plants of genus *Cannabis* are modified to produce CBDVA in controlled levels.

As used herein, the term "CBC" refers to cannabichromene and has the following structural formula:

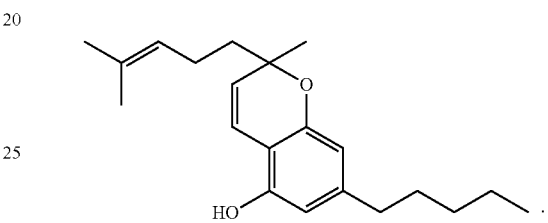

Within the context of this disclosure, plants of genus *Cannabis* are modified to produce CBC in controlled levels.

As used herein, the term "CBCA" refers to cannabichromenic acid and has the following structural formula:

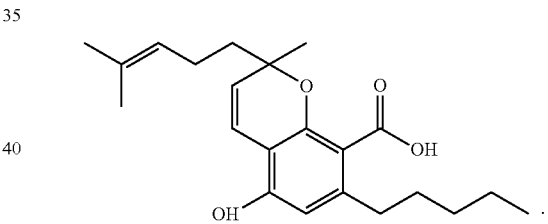

Decarboxylating CBCA with heat, light, etc., forms CBC and other possible cannabinoid derivatives. Within the context of this disclosure, plants of genus *Cannabis* are modified to produce CBCA in controlled levels.

As used herein, the term "CBCV" refers to cannabichromevarin and has the following structural formula:

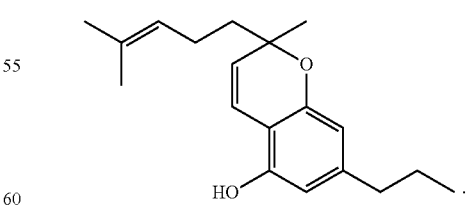

Within the context of this disclosure, plants of genus *Cannabis* are modified to produce CBCV in controlled levels.

As used herein, the term "CBCVA" refers to cannabichromevarinic acid and has the following structural formula:

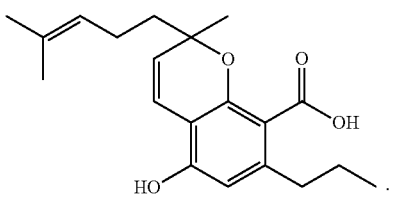 [SMILES: CCCc1cc(O)c2c(c1C(=O)O)OC(C)(CCC=C(C)C)C=C2]

Decarboxylating CBCVA with heat, light, etc., forms CBCV and other possible cannabinoid derivatives. Within the context of this disclosure, plants of genus *Cannabis* are modified to produce CBCVA in controlled levels.

As used herein, the term "CBG" refers to cannabigerol and has the following structural formula:

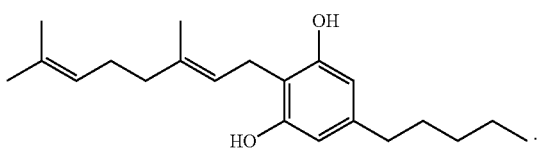 [SMILES: CCCCCc1cc(O)c(C/C=C(\C)CCC=C(C)C)c(O)c1]

Within the context of this disclosure, plants of genus *Cannabis* are modified to produce CBG in controlled levels.

As used herein, the term "CBGA" refers to cannabigerolic acid and has the following structural formula:

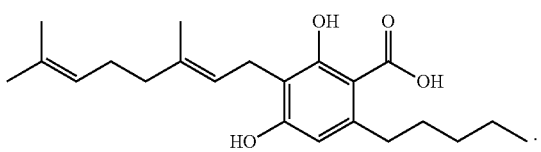 [SMILES: CCCCCc1cc(O)c(C/C=C(\C)CCC=C(C)C)c(O)c1C(=O)O]

Decarboxylating CBGA with heat, light, etc., forms CBG and other possible cannabinoid derivatives. Within the context of this disclosure, plants of genus *Cannabis* are modified to produce CBGA in controlled levels.

As used herein, the term "CBGV" refers to cannabigerovarin and has the following structural formula:

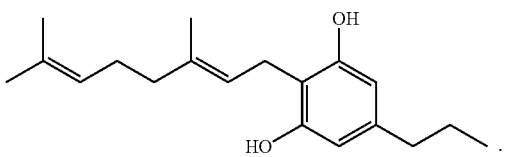 [SMILES: CCCc1cc(O)c(C/C=C(\C)CCC=C(C)C)c(O)c1]

Within the context of this disclosure, plants of genus *Cannabis* are modified to produce CBGV in controlled levels.

As used herein, the term "CBGVA" refers to cannabigerovarinic acid and has the following structural formula:

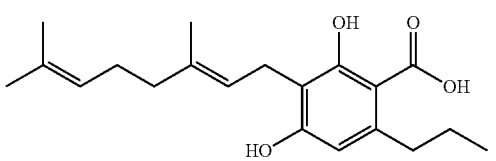

Decarboxylating CBGVA with heat, light, etc., forms CBGV and other possible cannabinoid derivatives. Within the context of this disclosure, plants of genus *Cannabis* are modified to produce CBGVA in controlled levels.

As used herein, the term "CBN" refers to cannabinol and has the following structural formula:

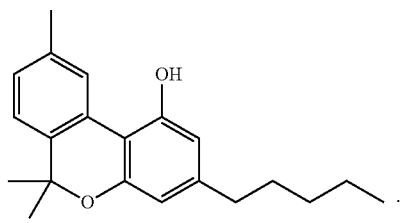 [SMILES: CCCCCc1cc(O)c2c(c1)OC(C)(C)c1ccc(C)cc1-2]

Within the context of this disclosure, plants of genus *Cannabis* are modified to produce CBN in controlled levels.

As used herein, the term "CBNA" refers to cannabinolic acid and has the following structural formula:

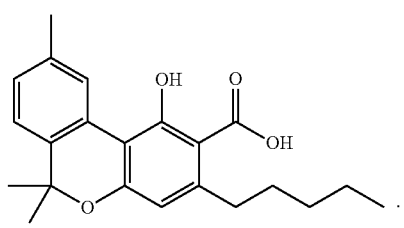 [SMILES: CCCCCc1cc2c(c(O)c1C(=O)O)-c1cc(C)ccc1C(C)(C)O2]

Decarboxylating CBNA with heat, light, etc., forms CBN and other possible cannabinoid derivatives. Within the context of this disclosure, plants of genus *Cannabis* are modified to produce CBNA in controlled levels.

As used herein, the term "CBNV" or "CBV" refers to cannabivarin and has the following structural formula:

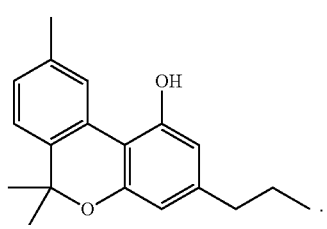 [SMILES: CCCc1cc(O)c2c(c1)OC(C)(C)c1ccc(C)cc1-2]

Within the context of this disclosure, plants of genus *Cannabis* are modified to produce CBNV in controlled levels.

As used herein, the term "CBNVA" refers to cannabivarinic acid and has the following structural formula:

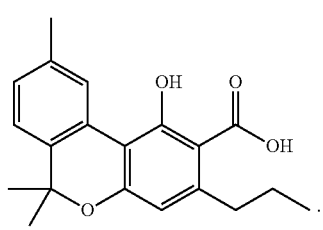 [SMILES: CCCc1cc2c(c(O)c1C(=O)O)-c1cc(C)ccc1C(C)(C)O2]

Decarboxylating CBNVA with heat, light, etc., forms CBNV and other possible cannabinoid derivatives. Within the context of this disclosure, plants of genus *Cannabis* are modified to produce CBNVA in controlled levels.

As used herein, the term "CBND" refers to cannabinodiol and has the following structural formula:

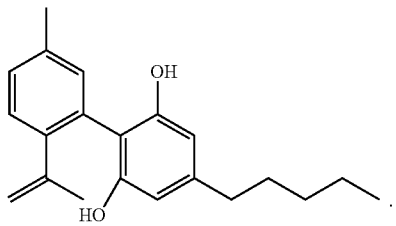 [SMILES: C=C(C)c1ccc(C)cc1-c1c(O)cc(CCCCC)cc1O]

Within the context of this disclosure, plants of genus *Cannabis* are modified to produce CBND in controlled levels.

As used herein, the term "CBNDA" refers to cannabinodiolic acid and has the following structural formula:

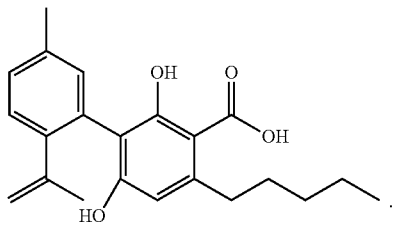 [SMILES: C=C(C)c1ccc(C)cc1-c1c(O)cc(CCCCC)c(C(=O)O)c1O]

Decarboxylating CBNDA with heat, light, etc., forms CBND and other possible cannabinoid derivatives. Within the context of this disclosure, plants of genus *Cannabis* are modified to produce CBNDA in controlled levels.

As used herein, the term "CBNDV" refers to cannabivarinodiol and has the following structural formula:

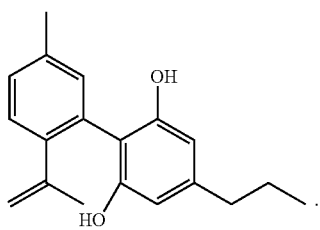 [SMILES: C=C(C)c1ccc(C)cc1-c1c(O)cc(CCC)cc1O]

Within the context of this disclosure, plants of genus *Cannabis* are modified to produce CBNDV in controlled levels.

As used herein, the term "CBNDVA" refers to cannabivarinodiolic acid and has the following structural formula:

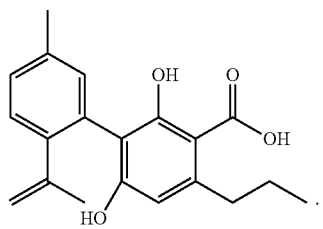 [SMILES: C=C(C)c1ccc(C)cc1-c1c(O)cc(CCC)c(C(=O)O)c1O]

Decarboxylating CBNDVA with heat, light, etc., forms CBNDV and other possible cannabinoid derivatives. Within the context of this disclosure, plants of genus *Cannabis* are modified to produce CBNDVA in controlled levels.

As used herein, the term "CBL" refers to cannabicyclol and has the following structural formula:

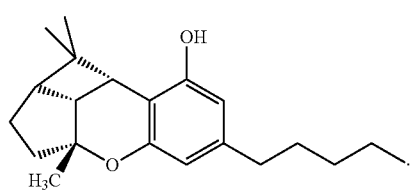

Within the context of this disclosure, plants of genus *Cannabis* are modified to produce CBL in controlled levels.

As used herein, the term "CBLA" refers to cannabicyclolic acid and has the following structural formula:

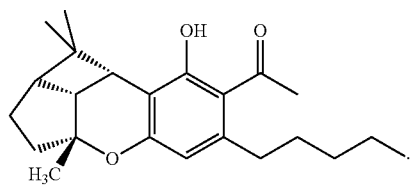

Decarboxylating CBLA with heat, light, etc., forms CBL and other possible cannabinoid derivatives. Within the context of this disclosure, plants of genus *Cannabis* are modified to produce CBLA in controlled levels.

As used herein, the term "CBLV" refers to cannabicyclovarin and has the following structural formula:

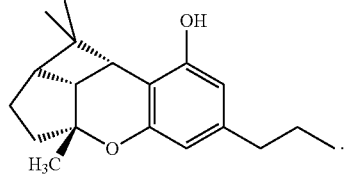

Within the context of this disclosure, plants of genus *Cannabis* are modified to produce CBLV in controlled levels.

As used herein, the term "CBLVA" refers to cannabielvarinsoinic acid and has the following structural formula:

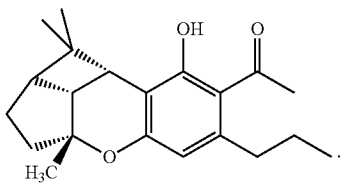

Decarboxylating CBLVA with heat, light, etc., forms CBLV and other possible cannabinoid derivatives. Within the context of this disclosure, plants of genus *Cannabis* are modified to produce CBLVA in controlled levels.

As used herein, the term "CBE" refers to cannabielsoin and has the following structural formula:

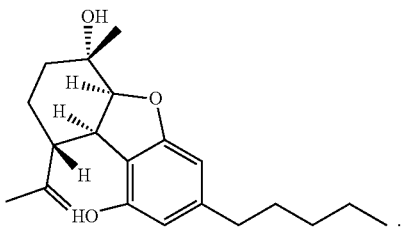

Within the context of this disclosure, plants of genus *Cannabis* are modified to produce CBE in controlled levels.

As used herein, the term "CBEA" refers to cannabielsoic acid and has the following structural formula:

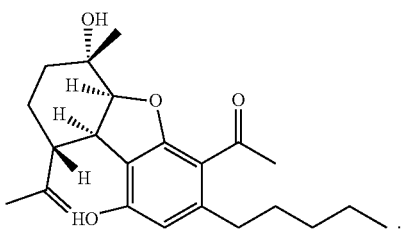

Decarboxylating CBEA with heat, light, etc., forms CBE and other possible cannabinoid derivatives. Within the context of this disclosure, plants of genus *Cannabis* are modified to produce CBEA in controlled levels.

As used herein, the term "CBEV" refers to cannabivarinselsoin and has the following structural formula:

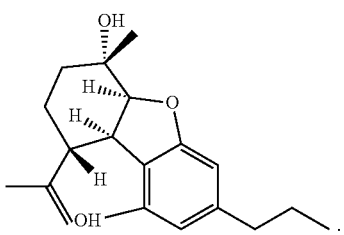

Within the context of this disclosure, plants of genus *Cannabis* are modified to produce CBEV in controlled levels.

As used herein, the term "CBEVA" refers to cannabivarinselsoinic acid and has the following structural formula:

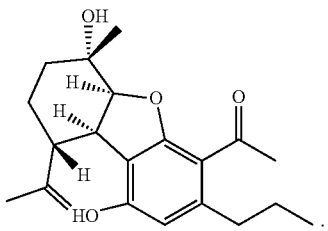

Decarboxylating CBEVA with heat, light, etc., forms CBEV and other possible cannabinoid derivatives. Within the context of this disclosure, plants of genus *Cannabis* are modified to produce CBEVA in controlled levels.

As used herein, the term "dry weight" refers to the mass of a sample after removing substantially all of the water within the sample. Any method suitable for removing water is acceptable. Exemplary methods of removing water include: placing the plant in a dehydrator, placing the plant in an oven, placing a desiccant with the plant in a container, and/or placing the plant under a lamp.

In one example, a plant is crushed and the number of structurally distinct compounds are determined. In one embodiment, the abundance, e.g., mass percent or number of compounds, of the sample is determined by techniques known in the art. Exemplary techniques for determining abundance, e.g., mass percent or number of compounds, include thin layer chromatography, high performance liquid chromatography, gas chromatography, gas chromatography mass spectrometry, supercritical fluid chromatography, etc.

In one embodiment, calculating the percentage by dry weight for a compound within a mixture (such a first cannabinoid within a dried flower after removing substantially all of the water) is accomplished with the following formula:

$$(\text{Total mass of first cannabinoid} = \text{Total mass of sample after removing water}) * 100\%$$

As used herein, the term "genome" refers to the complete sequence of genetic material of an organism. The genome of an organism contains all of the necessary information for building the organism through natural processes and reactions within the organism. Changing or modifying certain parts of the genome affects how the organism expresses certain features or characteristics. In one embodiment, the genome of an organism is changed to produce a first cannabinoid in an unnaturally occurring ratio with respect to the total cannabinoid content. In one embodiment, the genome of an organism is changed to produce a first cannabinoid in an unnaturally occurring ratio with respect to a second cannabinoid. In one embodiment, the genome of an organism is changed to produce a first cannabinoid in an unnaturally occurring concentration within a plant of genus *Cannabis*.

As used herein, the term "genetic material" refers to information found in an organism directing and/or dictating biological processes within the organism. Genetic material comprises RNA, DNA, any structures composed of DNA and/or RNA, e.g., genes, proteins, etc., derivatives of DNA and/or RNA, e.g., mRNA, cDNA, etc., or any combination thereof. The genome of an organism contains all the necessary information for building the organism through natural processes and reactions within the organism.

As used herein, the term "modified genetic material" refers to genetic material that is changed from the naturally occurring genetic material, e.g., DNA and/or RNA, coding or noncoding. In one embodiment, the modified genetic material is mutated DNA. In one embodiment, the modified genetic material is an altered genetic sequence corresponding to an enzyme.

As used herein, the term "CBCA synthase" refers to an enzyme acting as a catalyst for converting CBGVA into CBCVA and/or CBGA into CBCA.

As used herein, the term "CBCA synthase expression gene" refers to a gene coding for the enzyme CBCA synthase.

As used herein, the term "CBDA synthase" refers to an enzyme acting as a catalyst for converting CBGVA into CBDVA and/or CBGA into CBDA.

As used herein, the term "CBDA synthase expression gene" refers to a gene coding for the enzyme CBDA synthase.

As used herein, the term "THCA synthase" refers to an enzyme acting as a catalyst for converting CBGVA into THCVA and/or CBGA into THCA.

As used herein, the term "THCA synthase expression gene" refers to a gene coding for the enzyme THCA synthase.

As used herein, the term "olivetolic acid cyclase" refers to an enzyme acting as a catalyst for forming olivetolic acid.

As used herein, the term "tetraketide synthase" refers to an enzyme acting as a catalyst for forming olivetolic acid.

As used herein, the term "aromatic prenyltransferase" refers to an enzyme acting as a catalyst for converting precursor substrates into CBGA and/or CBGVA. In one embodiment, the precursor substrates are olivetolic acid and geranyl diphosphate. In one embodiment, the precursor substrates are divarinolic acid and germany diphosphate.

As used herein, the term "olivetolic acid" refers to a compound of the following structural formula:

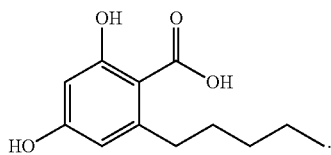 [SMILES: CCCCCc1cc(O)cc(O)c1C(=O)O ; "."]

Olivetolic acid is involved in the biosynthesis of CBGA, wherein olivetolic acid is combined with geranyl diphosphate via prenyltransferase enzymes. In one embodiment, the prenyltransferase enzyme is aromatic prenyltransferase.

As used herein, the term "divarinolic acid" refers to a compound of the following structural formula:

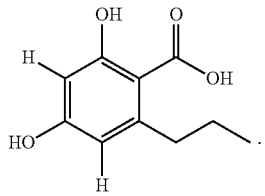

Divarinolic acid is involved in the biosynthesis of CBGVA, wherein divarinolic acid is combined with geranyl diphosphate via prenyltransferase enzymes. In one embodiment, the prenyltransferase enzyme is aromatic prenyltransferase.

In one embodiment, the plants disclosed herein comprise modified genetic material wherein the modified genetic material comprises a nucleic acid sequence coding for a cannabinoid synthesis enzyme.

As used herein, the term "nucleic acid sequence" refers to a series of nucleotides coupled together via covalent bonds. Nucleic acid sequences are often represented by a series of letters with each letter representing an individual nucleotide. In one embodiment, the nucleotides for RNA are U for uracil, G for guanine, C for cytosine, and A for adenine. In one embodiment, the nucleotides for DNA are T for thymine, G for guanine, C for cytosine, and A for adenine.

In one embodiment, the nucleic acid sequence codes for a functional protein. In one embodiment, the nucleic acid sequence does not code for a functional protein. In one embodiment, the nucleic acid sequence indicates the order of nucleotides within DNA. In one embodiment, the nucleic acid sequence indicates the order of nucleotides within RNA. Within the art, when referring to a nucleic acid sequence the term "nucleotide sequence" may also be used interchangeably.

As used herein, the term "cannabinoid synthesis enzyme" refers to a protein acting as a catalyst for producing one or more cannabinoids in a plant of genus Cannabis.

Examples of cannabinoid synthesis enzymes within the context of this disclosure include, but are not limited to: polyketide synthase (PKS), olivetolic acid cyclase (OAC), tetraketide synthase (TKS), type III PKS, chalcone synthase (CHS), prenyltransferase, THCA synthase, CBDA synthase, CBCA synthase, GPP synthase, FPP synthase, Limonene synthase, aromatic prenyltransferase, and geranylphosphate: olivetolate geranyltrasferase.

Disclosed herein, is a method of controlling cannabinoid synthesis in a plant of genus Cannabis, comprising:

Manipulating expression of a gene coding for a cannabinoid synthesis enzyme.

As used herein, the term "controlling" refers to directing, governing, steering, and/or manipulating the amount of a cannabinoid or cannabinoids produced in a plant of genus Cannabis. In one embodiment, controlling comprises modifying a plant of genus Cannabis to produce an unnaturally occurring concentration of a first cannabinoid. In one embodiment, controlling comprises modifying a plant of genus Cannabis to produce an unnaturally occurring ratio of a first cannabinoid. In one embodiment, controlling comprises modifying a plant of genus Cannabis to produce an unnaturally occurring concentration of a second cannabinoid. In one embodiment, controlling comprises modifying a plant of genus Cannabis to produce an unnaturally occurring ratio of a second cannabinoid.

As used herein, the term "expression of a gene" refers to a plant's ability to utilize information from genetic material for producing functional gene products. Within the context of this disclosure, expression is meant to encompass the plant's ability to produce proteins, such as enzymes, and various other molecules from the plant's genetic material. In one embodiment, the plant expresses cannabinoid synthesis enzymes for cannabinoid biosynthesis. In one embodiment, the plant makes RNA from a DNA template.

As used herein, the term "manipulating expression of a gene" refers to intentionally changing the genome of a plant of genus Cannabis to control the expression of certain features.

In one embodiment, the plant's genome is manipulated to express less CBDA synthase. In one embodiment, the plant's genome is manipulated to express less THCA synthase. In one embodiment, the plant's genome is manipulated to express less CBCA synthase. In one embodiment, the plant's genome is manipulated to express less olivetolic acid cyclase. In one embodiment, the plant's genome is manipulated to express less tetraketide synthase. In one embodiment, the plant's genome is manipulated to express less aromatic prenyltransferase.

In one embodiment, the plant's genome is manipulated to express more CBDA synthase. In one embodiment, the plant's genome is manipulated to express more THCA synthase. In one embodiment, the plant's genome is manipulated to express more CBCA synthase. In one embodiment, the plant's genome is manipulated to express more olivetolic acid cyclase. In one embodiment, the plant's genome is manipulated to express more tetraketide synthase. In one embodiment, the plant's genome is manipulated to express more aromatic prenyltransferase.

As used herein, the term "coding" refers to storing genetic information and accessing the genetic information for producing functional gene products. In one embodiment, a gene is coding for a protein. In one embodiment, a gene is coding for a catalyst. In one embodiment, a strand of DNA includes genetic material that is coding for rate of growth of a plant of genus *Cannabis*. In one embodiment, a strand of mRNA is coding for a protein, such as a cannabinoid synthesis enzyme.

In one embodiment, the methods disclosed herein comprise:
Selecting a first plant of genus *Cannabis*;
Selecting a second plant of genus *Cannabis*, wherein the first plant of genus *Cannabis* produces a first cannabinoid more than the second plant of genus *Cannabis*;
Collecting genetic material from the first plant of genus *Cannabis*;
Collecting genetic material from the second plant of genus *Cannabis*;
Comparing the genetic material from the first plant of genus *Cannabis* with the genetic material from the second plant of genus *Cannabis*; and
Identifying a difference in a gene sequence present within the genetic material from the first plant of genus *Cannabis* homologous to a gene sequence present within the genetic material from the second plant of genus *Cannabis*.

As used herein, the term "selecting a first plant of genus *Cannabis*" refers to choosing a plant of genus *Cannabis* producing a particular amount of a first cannabinoid measured by dry weight. In one embodiment, the methods disclosed herein comprises selecting a second plant of genus *Cannabis*. In one embodiment, selecting comprises choosing a plant of genus *Cannabis* by quantitative analysis of a crude extract, HPLC, Spectrometry techniques, etc.

In one embodiment, the first plant of genus *Cannabis* is from a different species than the second plant of genus *Cannabis*. In one embodiment, the first plant of genus *Cannabis* is from the same species as the second plant of genus *Cannabis*. In one embodiment, the first plant of genus *Cannabis* is from a different strain than the second plant of genus *Cannabis*. In one embodiment, the first plant of genus *Cannabis* is from the same strain as the second plant of genus *Cannabis*. In one embodiment, the first plant of genus *Cannabis* is from the same ancestor as the second plant of genus *Cannabis*. In one embodiment, the first plant of genus *Cannabis* is from the same parent as the second plant of genus *Cannabis*. In one embodiment, the first plant of genus *Cannabis* is from the same genus as the second plant of genus *Cannabis*. In one embodiment, the first plant of genus *Cannabis* is from a different genus than the second plant of genus *Cannabis*.

As used herein, the term "collecting genetic material" refers to gathering information found in an organism directing and/or dictating biological processes within the organism. In one embodiment, collecting genetic material comprises extracting a crude extract from a plant of genus *Cannabis*. Examples of extraction include, but are not limited to, organic extraction methods, filter based spinned basket formats, magnetic particle methods, liquid to liquid extraction, and direct lysis methods. In one embodiment, collecting genetic material comprises extracting RNA. In one embodiment, collecting genetic material comprises extracting DNA.

In one embodiment, collecting genetic material comprises making an aqueous solution of plant material from a plant of genus *Cannabis*, mixing the aqueous solution with water saturated phenol and chloroform, and putting the sample through a centrifuge to form an upper aqueous phase and lower organic phase. In one embodiment, a denaturing agent, e.g., guanidinium thiocyanate, is added to denature proteins resulting in the nucleic acids partitioning in the aqueous phase and proteins partitioning into the organic phase. In one embodiment, pH determines which nucleic acids get purified and the desired nucleic acids are precipitated with an alcohol.

In one embodiment, the methods disclosed herein comprise sequencing the genetic information.

As used herein, the term "sequencing the genetic information" refers to determining the presence, quantity, and/or order of nucleotides and/or nucleic acids in a biological sample. In one embodiment, sequencing the genetic material facilitates the ability to look at alternative gene spliced transcripts, post-transcriptional modifications, gene fusion, mutations/SNPs, and changes in gene expression. In one embodiment, sequencing the genetic information determines the RNA sequence. In addition to mRNA transcripts, sequencing RNA can provide information about populations of RNA to include total RNA, small RNA, such as miRNA, tRNA, rRNA, and ribosomal profiling. In one embodiment, sequencing the genetic information determines the DNA sequence.

As used herein, the term "identifying a difference" refers to finding a variation in the genetic material. For example, identifying a difference between a first plant of genus *Cannabis* and a second plant of genus *Cannabis*. In one embodiment, identifying the difference comprises finding a genetic sequence coding for an enzyme between a first plant of genus *Cannabis* and a second plant of genus *Cannabis*. In one embodiment, identifying a difference comprises finding the genetic material for trichome development between a first plant of genus *Cannabis* and a second plant of genus *Cannabis*.

As used herein, the term "homologous" refers to different versions of genetic material coding for a feature from a common ancestor. In one embodiment, a first plant of genus *Cannabis* and a second plant of genus *Cannabis* share a common ancestor but have different genes. In one embodiment, a first plant of genus *Cannabis* and a second plant of genus *Cannabis* share a common ancestral gene sequence with identifiable sequence level differences.

As used herein, the term "analogous" refers to different versions of genetic material coding for the same function but with non-overlapping ancestry. In one embodiment, a bacterium develops a resistance to an antibiotic via two genetically independent mechanisms at two independent times. Within the field of genetics, deep ancestral homology and horizontal gene transfer confuse the absolute correctness of when to use one term and not the other. Thus, within the context of this disclosure both terms are acceptable.

In one embodiment, the methods disclosed herein comprise comparing an assembled transcriptome of the first plant of genus *Cannabis* with an assembled transcriptome of the second plant of genus *Cannabis*.

As used herein, the term "transcriptome" refers to the sequence of messenger RNA expressed in one cell or a population of cells. In one embodiment, the genes associated with producing secondary compounds are identical with the assembled transcriptome of the plant of genus *Cannabis*.

As used herein, the term "assembled transcriptome" means gathering data about the RNA sequences used in protein synthesis within a cell or a population of cells. In one embodiment, if the assembly were theoretically perfect, it would consist of all RNA present in a given tissue sample. Within the context of this disclosure, the transcriptome may consist of one or more sequences. Within the context of this disclosure, the assembled transcriptome for harvested plants of genus *Cannabis* comprises thousands to millions of sections of RNA chunks, segments, or pieces. Furthermore, these small fragments can make larger scaffolds and contigs of genetic sequences.

As used herein, the term "comparing abundance of genes" refers to an analysis of the RNA sequence of the first plant in relation to the RNA sequence of the second plant. In one embodiment, comparing the abundance of genes includes comparing the fold change. In one embodiment, the fold change is used to measure the change in the expression level of genes. In one embodiment, the fold change is measured by RPKM.

As used herein, the term "RPKM" refers to "Reads Per Kilobase per Million mapped reads". The term RPKM refers to a method of quantifying gene expression from RNA sequencing data by normalizing for total read length and the number of sequencing reads. In one embodiment, RPKM calculation provides a normalization for comparing gene coverage values. The RPKM value corrects for differences in both sample sequencing depth and gene length.

In one example, the RPKM can be calculated via the following formula:

$$\text{numReads}/(\text{geneLength}/1000*\text{totalNumReads}/1{,}000{,}000);$$

wherein, "numReads" refers to the number of reads mapped to a gene sequence;

wherein, "geneLength" refers to the length of the gene sequence; and wherein, "totalNumReads" refers to the total number of mapped reads of a sample.

For example, the fold change data of a sample of CBG compared to a sample of CBGV for purely hypothetical and illustrative purposes could demonstrate the following relationship:

gene A: 2×
gene B: 1×
gene C: 1000×
gene D: 1.3×
gene E: 100×

In the illustrative example above, Gene C would be most likely to explain the phenotype difference and gene E the second most likely because of the relative abundance of reads.

The calculations required to perform the above comparison may be made via software available in the art, such as the Trinity workflow or a variety of other similar packages. RPKM is one method, other methods include, but are not limited to, Fragments Per Kilobase per Million mapped reads (FPKM) and Transcripts Per Kilobase Million (TPM).

In one embodiment, the methods disclosed herein comprise comparing a first gene sequence from the assembled transcriptome of the first plant of genus *Cannabis* to a second gene sequence from the assembled transcriptome of the second plant of genus *Cannabis*.

As used herein, the term "comparing" refers to analyzing the first gene sequence with the second gene sequence to determine the differences and similarities of the two sets of gene sequences.

In one embodiment, the methods disclosed herein comprise identifying at least one gene that is expressed more within the first plant of genus *Cannabis* compared to the second plant of genus *Cannabis*.

As used herein, the term "expressed more" means a gene that is present in two plants' genome and the gene in one plant is regulated to produce greater units of functional proteins or gene products from the gene in question (aka up-regulated) compared to the gene in the other plant.

In one embodiment, the method disclosed herein comprises identifying at least one gene that is expressed less within the first plant of genus *Cannabis* compared to the second plant of genus *Cannabis*.

As used herein, the term "expressed less" means a gene that is present in both plants' genome and the gene in one plant is regulated to produce fewer units of functional proteins or gene products from the gene in question (aka down-regulated) as compared to the gene in the other plant.

As used herein, the term "regulated" means modifying or affecting the genetic mechanisms of protein or RNA expression that further dictate the expression of genes. In one embodiment, gene expression is regulated through the introduction of promoters and/or other regulatory elements such as enhancers and repressors that increase transcription of proteins. In one embodiment, gene expression is regulated by increasing translation of mRNA.

In one embodiment, the methods disclosed herein comprise comparing an expressed number of a gene sequence found in each of A) the assembled transcriptome of the first plant of genus *Cannabis* and B) the assembled transcriptome of the second plant of genus *Cannabis*.

As used herein, the term "expressed number" refers to the number of times a gene is transcribed to make mRNA, and ultimately for making functional proteins. In one embodiment, expressed number can determine how many times a cannabinoid synthesis gene is expressed.

As used herein, the term "cannabinoid synthesis gene" refers to genetic material coding for a protein and/or enzyme involved in producing secondary compounds, e.g., a cannabinoid or cannabinoids, found in a plant of genus *Cannabis*.

In one embodiment, the cannabinoid synthesis gene codes for CBCA synthase. In one embodiment, the cannabinoid synthesis gene codes for CBDA synthase. In one embodiment, the cannabinoid synthesis gene codes for THCA synthase. In one embodiment, the cannabinoid synthesis gene codes for tetraketide synthase. In one embodiment, the cannabinoid synthesis gene codes for aromatic prenyltransferase. In one embodiment, the cannabinoid synthesis gene codes for olivetolic acid cyclase.

In one embodiment, the methods disclosed herein comprise identifying the expressed number of a CBCA synthase expression gene. In one embodiment, the methods disclosed herein comprise identifying the expressed number of a CBDA synthase expression gene. In one embodiment, the methods disclosed herein comprise identifying the expressed number of a THCA synthase expression gene. In one embodiment, the methods disclosed herein comprise identifying the expressed number of an aromatic prenyltransferase expression gene. In one embodiment, the methods disclosed herein comprise identifying the expressed number of a tetraketide synthase expression gene. In one embodiment, the methods disclosed herein comprise identifying the expressed number of an olivetolic acid cyclase expression gene.

In one embodiment, the methods disclosed herein comprise comparing an abundance of gene copies of the assembled transcriptome of the first plant to an abundance of gene copies of the assembled transcriptome of the second plant.

In one embodiment, the methods disclosed herein comprise identifying at least one gene expressed more in the first plant of genus *Cannabis* compared to second plant of genus *Cannabis*.

In one embodiment, the methods disclosed herein comprise identifying at least one gene expressed less in the first plant of genus *Cannabis* compared to second plant of genus *Cannabis*.

In one embodiment, the methods disclosed herein comprise overexpressing at least one gene expressed less in the first plant of genus *Cannabis* compared to second plant of genus *Cannabis*.

In one embodiment, the methods disclosed herein comprise underexpressing at least one gene expressed less in the first plant of genus *Cannabis* compared to second plant of genus *Cannabis*.

In one embodiment, the methods disclosed herein comprise overexpressing at least one gene expressed more in the first plant of genus *Cannabis* compared to second plant of genus *Cannabis*.

In one embodiment, the methods disclosed herein comprise underexpressing at least one gene expressed more in the first plant of genus *Cannabis* compared to second plant of genus *Cannabis*.

In one embodiment, the methods disclosed herein comprise overexpressing at least one gene expressed more in the first plant of genus *Cannabis* compared to second plant of genus *Cannabis*; and underexpressing at least one gene expressed less in the first plant of genus *Cannabis* compared to second plant of genus *Cannabis*.

In one embodiment, the methods disclosed herein comprise comparing a genome of the first plant of genus *Cannabis* with a genome of the second plant of genus *Cannabis*.

In one embodiment, the methods disclosed herein comprise comparing copy number of a gene sequence found in each of A) the genome of the first plant of genus *Cannabis* and B) the genome of the second plant of genus *Cannabis*.

As used herein, the term "copy number" refers to how many times a specific sequence is repeated in the genome. In one embodiment, comparing DNA sequences may determine which plant has a lower copy number of a sequence coding for CBCA synthase. In one embodiment, comparing DNA sequences may determine which plant has a lower copy number of a sequence coding for CBDA synthase. In one embodiment, comparing DNA sequences may determine which plant has a lower copy number of a sequence coding for THCA synthase.

In one embodiment, the methods disclosed herein comprise comparing an abundance of gene sequences of the assembled genome of the first plant of genus *Cannabis* to an abundance of gene sequences of the assembled genome of the second plant of genus *Cannabis*.

In one embodiment, the methods disclosed herein comprise identifying at least one gene present with more copies in the genome of the first plant of genus *Cannabis* than in the genome of the second plant of genus *Cannabis*.

In one embodiment, the methods disclosed herein comprise identifying at least one gene present with less copies in the genome of the first plant of genus *Cannabis* than in the genome of the second plant of genus *Cannabis*.

In one embodiment, the methods disclosed herein comprise overexpressing a gene sequence present within the genetic material of the first plant of genus *Cannabis* homologous to a gene sequence present within the genetic material of the second plant of genus *Cannabis*.

In one embodiment, the methods disclosed herein comprise underexpressing a gene sequence present within the genetic material of the first plant of genus *Cannabis* homologous to a gene sequence present within the genetic material of the second plant of genus *Cannabis*.

In one embodiment, the methods disclosed herein comprise underexpressing a gene sequence present within the genetic material of the first plant of genus *Cannabis* homologous to a gene sequence present within the genetic material of the second plant of genus *Cannabis*; and overexpressing a gene sequence present within the genetic material of the first plant of genus *Cannabis* homologous to gene sequence present within the genetic material of the second plant of genus *Cannabis*.

As used herein, the term "overexpressing" refers to increasing the activity of a gene in one plant of genus *Cannabis* resulting in the production of more functional units of proteins and/or gene products. In one embodiment, overexpressing comprises introducing promoters, adding genes, and/or inhibiting repressors.

As used herein, the term "underexpressing" refers to decreasing the activity of gene in one plant resulting in the production of less functional units of proteins and/or gene products. In one embodiment, underexpressing comprises introducing repressors, deleting genes, and/or promoting genes responsible for repression.

In one embodiment, the methods disclosed herein comprise a difference of a gene sequence present within the genetic material from the first plant of genus *Cannabis* homologous to a gene sequence present within the genetic material from the second plant of genus *Cannabis*, wherein the difference is a gene sequence coding for a cannabinoid synthesis enzyme.

In one embodiment, the cannabinoid synthesis enzyme is chosen from one of THCA synthase, CBCA synthase, CBDA synthase, aromatic prenyltransferase, olivetolic acid cyclase, or tetraketide synthase.

In one embodiment, the methods disclosed herein comprise overexpressing the gene sequence coding for a cannabinoid synthesis enzyme. In one embodiment, the methods disclosed herein comprise overexpressing the gene sequence coding for aromatic prenyltransferase. In one embodiment, the methods disclosed herein comprise overexpressing the gene sequence coding for CBCA synthase. In one embodiment, the methods disclosed herein comprise overexpressing the gene sequence coding for CBDA synthase. In one embodiment, the methods disclosed herein comprise overexpressing the gene sequence coding for THCA synthase. In one embodiment, the methods disclosed herein comprise overexpressing the gene sequence coding for olivetolic acid cyclase. In one embodiment, the methods disclosed herein comprise overexpressing the gene sequence coding for tetraketide synthase.

In one embodiment, the methods disclosed herein comprise underexpressing the gene sequence coding for a cannabinoid synthesis enzyme. In one embodiment, the methods disclosed herein comprise underexpressing the gene sequence coding for aromatic prenyltransferase. In one embodiment, the methods disclosed herein comprise underexpressing the gene sequence coding for CBCA synthase. In one embodiment, the methods disclosed herein comprise underexpressing the gene sequence coding for CBDA synthase. In one embodiment, the methods disclosed herein comprise underexpressing the gene sequence coding for THCA synthase. In one embodiment, the methods disclosed herein comprise underexpressing the gene sequence coding for olivetolic acid cyclase. In one embodiment, the methods disclosed herein comprise underexpressing the gene sequence coding for tetraketide synthase.

In some embodiments, the methods disclosed herein comprise:
- Constructing an endonuclease enzyme targeting a nucleic acid sequence coding for cannabinoid synthesis enzymes;
- Introducing the endonuclease enzyme into a genome of a plant of genus *Cannabis*; and
- Manipulating expression of the cannabinoid synthesis enzymes within the genome.

As used herein, the term "endonuclease enzyme" refers to a molecule capable of cleaving phosphodiester bond within a polynucleotide chain. In one embodiment, the endonuclease enzyme cleaves phosphodiester bonds in a DNA strand. In one embodiment, the endonuclease enzyme cleaves phosphodiester bonds in a RNA strand. In one embodiment, the endonuclease enzyme is a CRISPR/Cas9 complex. In one embodiment, the endonuclease enzyme is a zinc finger nuclease.

As used herein, the term "constructing an endonuclease enzyme" refers to creating a molecule capable of cleaving phosphodiester bond within a polynucleotide chain for genetic modification. In one embodiment, constructing an endonuclease enzyme is intended for cleaving genes out of the genome. In one embodiment, cleaving results in a mutation of the DNA sequence rendering it nonfunctional for coding, e.g., making proteins. In one embodiment, constructing an endonuclease enzyme includes additional structures for assisting in cleaving. In one example, a guide RNA is incorporated.

As used herein, the term "cleaving" means breaking a chemical bond, or bonds, between two atoms resulting in separating the two atoms. Within the context of this disclosure, cleaving encompasses techniques known in the art and natural processes in an organism. In one example cleaving bonds comprises catabolism, breaking larger molecules into smaller subunits by oxidation. In one example cleaving bonds comprises hydrolysis.

As used herein, the term "targeting a nucleic acid sequence" refers to designing an endonuclease enzyme to recognize a specific sequence of nucleotides. Recognizing a specific sequence of nucleotides allows for precise, efficient, and flexible gene editing, e.g., by guiding/directing a small sequence of DNA, targeting specific genes, etc. In one embodiment, the nucleic acid sequence is a DNA sequence. In one embodiment, the nucleic acid sequence is a RNA sequence.

In one embodiment, targeting a nucleic acid sequence comprises directing an endonuclease enzyme to recognize a sequence of DNA coding for a cannabinoid synthesis enzyme.

In one embodiment, targeting a nucleic acid sequence comprises directing an endonuclease enzyme to recognize a sequence of DNA coding for CBCA synthase. In one embodiment, targeting a nucleic acid sequence comprises directing an endonuclease enzyme to recognize a sequence of DNA coding for CBDA synthase. In one embodiment, targeting a nucleic acid sequence comprises directing an endonuclease enzyme to recognize a sequence of DNA coding for THCA synthase. In one embodiment, targeting a nucleic acid sequence comprises directing an endonuclease enzyme to recognize a sequence of DNA coding for tetraketide synthase. In one embodiment, targeting a nucleic acid sequence comprises directing an endonuclease enzyme to recognize a sequence of DNA coding for aromatic prenyltransferase. In one embodiment, targeting a nucleic acid sequence comprises directing an endonuclease enzyme to recognize a sequence of DNA coding for olivetolic acid cyclase.

As used herein, the term "introducing the endonuclease enzyme" refers to adding the endonuclease enzyme into a plant of genus *Cannabis*. In one embodiment, introducing the endonuclease enzyme comprises utilizing in vivo techniques through transgenics. In one embodiment, the endonuclease enzyme is constructed in vitro and introduced into the genome of a plant of genus *Cannabis*.

As used herein, the term "in vivo" refers to a biological process or processes inside of a living organism. In one embodiment, the term "in vivo" refers to transgenics.

As used herein, the term "transgenics" is the introduction of manufactured genes into a living organism. Examples of transgenic techniques include, but are not limited to, biolistics, *Agrobacterium* mediated transformation, and protoplast transfection.

As used herein, the term "in vitro" refers to biological processes outside of a living organism. In one embodiment, the endonuclease enzyme is constructed in an artificial culture medium. In one embodiment, the artificial culture medium is a test tube. In one embodiment, the artificial culture medium is a petri dish. In one embodiment, the artificial culture medium is a flask. In one embodiment, a bacteria is made in vitro comprising a genetic sequence coding for an endonuclease enzyme.

In one embodiment, the endonuclease enzyme is made in vitro. In one embodiment, introducing the endonuclease enzyme is accomplished through inoculating the plant with a bacteria comprising a genetic sequence for an endonuclease enzyme. Once inoculated, the bacteria makes plant cells which will then produce the endonuclease enzyme. In one embodiment, inoculating comprises placing the plant in a vacuum chamber with a bacterial solution comprising the endonuclease enzyme and removing air drawing the bacterial solution comprising the endonuclease enzyme into the plan. In one embodiment, inoculating comprises spraying the plant with an endonuclease enzyme. In one embodiment, "spraying" includes biolistic particle bombardment.

In one embodiment, the endonuclease enzyme is a CRISPR/Cas9 system.

As used herein, the term "CRISPR" refers to an acronym that means Clustered Regularly Interspaced Short Palindromic Repeats of DNA sequences. CRISPR is a series of repeated DNA sequences with unique DNA sequences in between the repeats. RNA transcribed from the unique strands of DNA serves as guides for directing cleaving. CRISPR is used as a gene editing tool. In one embodiment, CRISPR is used in conjunction with a Cas9 protein.

As used herein, the term "Cas" refers to CRISPR associated proteins that act as enzymes cutting the genome at specific sequences. Cas9 refers to a specific group of proteins known in the art. RNA sequences made from CRISPR direct Cas9 enzymes to cut certain sequences found in the genome. Other classes of Cas are also acceptable. In one embodiment, the CRISPR/Cas9 system cleaves one or two chromosomal strands at known Cas9 protein domains. In one embodiment, one of the two chromosomal strands is mutated. In one embodiment, two of the two chromosomal strands are mutated.

As used herein, the term "chromosomal strand" refers to a sequence of DNA within the chromosome. When the CRISPR/Cas9 system cleaves the chromosomal strands, the strands are cut leaving the possibility of one or two strands being mutated, either the template strand or coding strand.

As used herein, the term "template strand of DNA" refers to the sequence of DNA used for synthesizing mRNA. In one embodiment, the template strand of DNA encodes a gene for a cannabinoid synthesis enzyme. In one embodiment, the cannabinoid synthesis enzyme is chosen from THCA synthase, CBCA synthase, CBDA synthase, tetraketide synthase, aromatic prenyltransferase, or aromatic prenyltransferase.

As used herein, the term "coding strand of DNA" refers to the sequence of DNA that corresponds to the codons, which are ultimately translated into proteins. In one embodiment, the coding strand of DNA encodes a gene for a cannabinoid synthesis enzyme. In one embodiment, the cannabinoid synthesis enzyme is chosen from THCA synthase, CBCA synthase, CBDA synthase, tetraketide synthase, aromatic prenyltransferase, or aromatic prenyltransferase.

In one embodiment, either strand of chromosomal DNA could be the "coding strand" or the "template strand". In one embodiment, the inherent structure of the DNA strand is relevant in determining which strand is the coding strand and which strand is the template strand.

As used herein, the term "mutated" means to change a nucleotide or nucleotides in a genetic sequence causing a change in the naturally occurring genetic sequence. The change in genetic sequence in turn affects the intended function of a protein or enzyme made from the genetic sequence. Alternative methods of DNA cutting or mutation include TALENS, zinc finger nucleases, etc.

In one embodiment, the CRISPR/Cas9 system cleaves both strands inducing non-homologous end joining (NHEJ) and then an insertion/deletion (INDEL) causing the protein to mutate and become nonfunctional. In one embodiment, the non-functionality results from a nonsense mutation that causes a premature stop codon.

In one embodiment, the CRISPR/Cas9 system cleaves both strands causing homology directed repair (HDR) to occur. In one embodiment, a donor DNA strand is inserted into the space between the cleaved strands preventing random mutation. In one embodiment, the donor DNA strand is a DNA sequence coding for aromatic prenyltransferase. In one embodiment, the donor strand is a noncoding DNA sequence.

In one embodiment, the methods disclosed herein comprise inserting a donor strand of DNA into the genome of the plant of genus *Cannabis*.

In one embodiment, the donor strand of DNA is a gene sequence coding for aromatic prenyltransferase.

As used herein, the term "donor strand of DNA" refers to genetic material inserted into the genome, a strand of DNA, a gene, etc. The donor strand of DNA may be coding or noncoding. In one embodiment, a donor strand of DNA is inserted into the cut sites of DNA to prevent mutations from occurring from DNA repair. In one embodiment, a donor strand of DNA is inserted into the cut sites of DNA to induce mutation.

In one embodiment, the methods disclosed herein comprise a RNA guide.

As used herein, the term "RNA guide" refers to a strand of RNA recognizing a specific sequence of genetic material and directing where the endonuclease enzyme to cut.

In one embodiment, the RNA guide directs the endonuclease enzyme to cleave chromosomal strands coding for a cannabinoid synthesis enzyme.

In one embodiment, the RNA guide directs the CRISPR/Cas9 system to cleave chromosomal strands coding for a cannabinoids synthesis enzyme.

In one embodiment, the RNA guide directs the CRISPR/Cas9 system to target a CBDA synthase expression gene. In one embodiment, the RNA guide directs the CRISPR/Cas9 system to target a CBCA synthase expression gene. In one embodiment, the RNA guide directs the CRISPR/Cas9 system to target a THCA synthase expression gene. In one embodiment, the RNA guide directs the CRISPR/Cas9 system to target an olivetolic acid cyclase expression gene. In one embodiment, the RNA guide directs the CRISPR/Cas9 system to target a tetraketide synthase expression gene.

Within the context of this disclosure, other examples of endonuclease enzymes include SpCas9 from Strptococcus pyrogenes and others. Additionally, SpCas9 have differing Protospacer Adjacent Motif (PAM) sequences from NGG, which may offer other advantages. In one example, a SpCas9 has a smaller coding sequence.

Other examples of proteins that work with CRISPRs or RNA guides include Cpf1, which can be used for cutting DNA strands with overhanging ends instead of blunt ends, or C2c2 for cutting RNA with an RNA guide.

As used herein, the term "PAM" refers to a short DNA base pair sequence immediately following the DNA sequence targeted by an endonuclease enzyme. In one embodiment, the endonuclease enzyme is a CRISPR/Cas9 system.

As used herein, the term "NGG" means a 3 nucleobase sequence with a variable followed by two Gs. "N" means any nucleobase while "G" means guanine nucleobases.

In one embodiment, the methods disclosed herein comprise an endonuclease enzyme and an RNA guide. In one embodiment, the methods disclosed herein comprise a guide RNA transcribed in vitro. In one embodiment, the methods disclosed herein comprise a guide RNA transcribed in vivo.

In one embodiment, the methods disclosed herein comprise introducing a Cas9 enzyme and guide RNA expression cassette into the genome.

In one embodiment, the CRISPR/Cas9 system cleaves a sequence of a functional THCA synthase expression gene. In one embodiment, the CRISPR/Cas9 system cleaves a sequence of a functional CBDA synthase expression gene. In one embodiment, the CRISPR/Cas9 system cleaves a sequence of a functional CBCA synthase expression gene. In one embodiment, the CRISPR/Cas9 system cleaves a sequence of a functional tetraketide synthase expression gene. In one embodiment, the CRISPR/Cas9 system cleaves a sequence of a functional olivetolic acid cyclase expression gene.

Within the context of this disclosure, cleaving a sequence of a functional gene causes a mutation, sequence change, rearrangement, etc., destroying or changing the functionality of an enzyme or protein expressed from the gene.

In one embodiment, the methods disclosed herein comprise manipulating the expression of enzymes within the genome by interfering with expression of cannabinoid synthesis genes.

As used herein, the term "interfering with expression" means hindering the ability of the genome to express functional gene products. In one embodiment, interfering with expression is accomplished via knockdown. In one embodiment, interfering with expression is accomplished via knockout.

As used herein, the term "knockout" refers to a process of functionally preventing genes coding for enzymes, proteins, molecules, and/or compounds. In one embodiment, knockout comprises a gene to not code for an enzyme. In one embodiment, a gene coding for a cannabinoid synthesis enzyme is functionally cut, e.g., mutation, changing a sequence, etc. In one embodiment, a gene coding for a cannabinoid synthesis enzyme is removed from a strand of DNA.

As used herein, the term "knockdown" refers to a process of interfering with the transcription, post transcription, pre-translation, translation, etc., of genetic information into enzymes, proteins, molecules, or compounds. In one embodiment, knockdown comprises the interference with genetic information involved in the biosynthesis of cannabinoids, e.g., genes coding for a cannabinoid synthesis enzyme.

In one embodiment, the methods disclosed herein comprise interfering with expression via RNAi.

As used herein, the term "RNAi" refers to RNA interference. RNAi is a method of gene silencing by interfering with messenger RNA, aka mRNA. In one embodiment, miRNA (microRNA) and siRNA (small interfering RNA) molecules bind to specific sequences of mRNA, degrading the mRNA, and preventing translation of certain proteins or enzymes. RNA induced silencing complexes (RISC) comprise an argonaute protein (a type of endonuclease enzyme), which cleaves the targeted mRNA.

In one embodiment, the methods disclosed herein comprise interfering with expression of cannabinoid synthesis enzyme. In one embodiment, the cannabinoid synthesis enzyme is CBCA synthase. In one embodiment, the cannabinoid synthesis enzyme is CBDA synthase. In one embodiment, the cannabinoid synthesis enzyme is THCA synthase. In one embodiment, the cannabinoid synthesis enzyme is tetraketide synthase. In one embodiment, the cannabinoid synthesis enzyme is olivetolic acid cyclase. In one embodiment, the methods disclosed herein comprise introducing additional copies of cannabinoid synthesis enzymes.

As used herein, the term "introducing additional copies" means adding more genes coding for particular copies of enzymes within the plant of genus *Cannabis*. In one embodiment, introducing additional copies comprises inoculating a plant of genus *Cannabis* with a CRISPR/Cas9 complex.

In one embodiment, additional copies of a cannabinoid synthesis gene are introduced into a plant of genus *Cannabis*. In one embodiment, additional copies of a cannabinoid synthesis gene are introduced into the plant's genome. In one embodiment, the cannabinoid synthesis gene codes for aromatic prenyltransferase. In one embodiment, the methods disclosed herein comprise increasing availability of precursor substrates.

As used herein, the term "precursor substrate" refers to a compound used for subsequent reactions and processes to produce other compounds. In one embodiment, CBGVA is a precursor substrate. In one embodiment, CBGVA is converted to form CBGV. In other embodiments, CBGVA is converted into THCVA, CBDVA, and/or CBCVA. In other embodiments, THCVA, CBDVA, and CBCVA are used as precursor substrates for subsequent reactions and processes.

Within the context of this disclosure, a precursor substrate may refer to any/all enzymes and/or proteins involved in the biosynthesis of cannabinoids. In one embodiment, aromatic prenyltransferase is a precursor substrate.

As used herein, the term "increasing availability of precursor substrates" refers to allowing more precursor substrates to react in subsequent reactions for creating other molecules and/or compounds. In one embodiment, the precursor substrate is CBGVA. In one embodiment, the methods disclosed herein comprise decarboxylating CBGVA. In one embodiment, the methods disclosed herein comprise decarboxylating CBGVA to form CBGV. In one embodiment, the precursor substrate is CBGA. In one embodiment, the methods disclosed herein comprise decarboxylating CBGA. In one embodiment, the methods disclosed herein comprise decarboxylating CBGA to form CBG.

In one embodiment, decarboxylating comprises heat. In one embodiment, decarboxylating comprises light.

Disclosed herein are plants produced by the methods disclosed herein. In one embodiment, the plants disclosed herein produce unnatural ratios of cannabinoids. In one embodiment, the plants disclosed herein produce unnatural concentrations of cannabinoids.

In one embodiment, a plant is produced by the method of controlling synthesis of a first cannabinoid in a plant of genus *Cannabis* comprising:
  manipulating expression of a gene coding for a cannabinoid synthesis enzyme.
In one embodiment, a plant is produced by the method of:
  Selecting a first plant of genus *Cannabis*;
  Selecting a second plant of genus *Cannabis*, wherein the first plant of genus *Cannabis* produces a first cannabinoid more than the second plant of genus *Cannabis*;
  Collecting genetic material from the first plant of genus *Cannabis*;
  Collecting genetic material from the second plant of genus *Cannabis*;
  Comparing the genetic material from the first plant of genus *Cannabis* with the genetic material from the second plant of genus *Cannabis*; and
  Identifying a difference in a gene sequence present within the genetic material from the first plant of genus *Cannabis* homologous to a gene sequence present within the genetic material from the second plant of genus *Cannabis*.
In one embodiment, a plant is produced by the method of:
  Constructing an endonuclease enzyme targeting a nucleic acid sequence coding for a cannabinoid synthesis enzyme;
  Introducing the endonuclease enzyme into a genome of the plant of genus *Cannabis; and*
  Manipulating expression of the cannabinoid synthesis enzyme within the genome.
In one embodiment, a plant is produced by the method of:
  Manipulating expression of a gene coding for a cannabinoid synthesis enzyme; comprising:
  Selecting a first plant of genus *Cannabis*;
  Selecting a second plant of genus *Cannabis*, wherein the first plant of genus *Cannabis* produces a first cannabinoid more than the second plant of genus *Cannabis*;
  Collecting genetic material from the first plant of genus *Cannabis*;

Collecting genetic material from the second plant of genus *Cannabis*;

Comparing the genetic material from the first plant of genus *Cannabis* with the genetic material from the second plant of genus *Cannabis*; and Identifying a difference in a gene sequence present within the genetic material from the first plant of genus *Cannabis* homologous to a gene sequence present within the genetic material from the second plant of genus *Cannabis*; and further comprising:

Constructing an endonuclease enzyme targeting nucleic acid sequence coding for a cannabinoid synthesis enzyme;

Introducing the endonuclease enzyme into a genome of the plant of genus *Cannabis*; and Manipulating expression of the cannabinoid synthesis enzyme within the genome.

EXAMPLES

Example 1

General considerations for the controlled synthesis of a cannabinoid in *Cannabis* sp. plants was accomplished via a multi-branched pathway. Enzymatic processes are responsible for each of the single branches. If the plant only produces a subset of these enzymes or gene products, the present multi-branched pathway may be specified for a single preferred synthesis product.

Example 2

Disclosed herein is an illustrative example of enhancing the production of CBGA as the single cannabinoid of interest within a plant of genus *Cannabis*. The synthesis of CBGA in *Cannabis* sp. plants takes place at an intermediate step in the process of synthesizing THCA, CBDA, and/or CBCA. CBGA specifically serves as substrate that is utilized by specific cannabinoid synthesis enzymes, e.g., THCA-synthase, CBDA-synthase, and CBCA-synthase. These enzymes are efficient in converting CBGA into terminal products. Therefore, CBGA is never present in abundance when these enzymes are present.

To enhance the production of CBGA, genomic editing techniques were used to reduce/eliminate the amount of functional cannabinoid synthesis enzymes produced within the plant. An alignment was made using mRNA sequences for THCA synthase, CBDA synthase, and CBCA synthase to find a CRISPR target sequence. These genes share significant amounts of sequence homology meaning a well-made alignment can cut the genes producing these enzymes simultaneously.

When the sequence homology site was identified, an RNA expression cassette was designed in silico and developed as a synthetic dsDNA construct. The RNA expression construct consisted of a constitutive Pol III promoter (*Arabidopsis thaliana* U6) driving expression of a sgRNA molecule containing the target of interest.

The synthetic dsDNA construct was ligated into an *Agrobacterium* plant transfection vector plasmid containing a second expression cassette. The second expression cassette confers expression of a eukaryotic codon optimized version of SpCas9 protein. The expression of SpCas9 is accomplished via a constitutively active CaMV35s promoter. The ligated plasmid containing both expression cassettes was transformed into *E. coli* and plated.

Single colonies were isolated and grown for subsequent extraction via minipreparation of plasmid DNA. The plasmid isolated from this procedure was checked via sequencing, PCR, and gel electrophoresis. A single plasmid sample was isolated and checked. The plasmid was transformed into *Agrobacterium tumefaciens*. Single colonies were isolated. The *Agrobacterium* strain harbors a disarmed Ti plasmid that confers the virulence function during *Agrobacterium* mediated plant transfection. Selection for both plasmids was performed with two antibiotics, one relevant to each plasmid. Colonies were doubly selected this way were grown to quantities required for plant inoculation with dual antibiotic treatment on LB media.

Example 3

Disclosed herein is an illustrative example of inoculation on a small scale with a bacteria or vector made by the dual antibiotic treatment made in Example 2.

*Agrobacterium* cells were collected from plates via scraping and suspended into inoculation media. The cells were resuspended to a target density of 0.02-0.5 $OD_{600}$. The inoculation fluid consisted of ¼ MS plant media, ½ AB salts (17.2 mM $K_2HPO_4$, 8.3 mM $NaH_2PO_4$, 18.7 mM $NH_4Cl$, 2 mM KCl), 0.3% sucrose, and 50 mM MES, 200 uM Acetosyringone at a pH of about 5.5. The cells were cultured in this inoculation mix for 2-6 hours at room temperature prior to plant inoculation.

Cuttings or newly rooted clones of *Cannabis sativa* were submerged upside down in the *Agrobacterium* inoculation mixture and placed in a vacuum chamber. A light vacuum of −5 Hg was applied to the submerged plants for 30 seconds and the vacuum was slowly released. The treated plants were either rooted via rooting hormone or simply grown if already rooted. The adult plants were scored for chemical composition weeks later.

The plants that resulted from these processes were intended to act both as production plants as well as vegetative propagation material for subsequent growth cycles.

Example 4

Disclosed herein is an illustrative example of inoculation on a large scale with a bacteria or vector made by the dual antibiotic treatment made in Example 2.

Adequate quantities of transformed *Agrobacterium* cells were grown on plates and harvested via scraping to produce 30 L of inoculation fluid at a density 0.02-0.1 $OD_{600}$. The inoculation fluid consisted of deionized water with an adjusted pH of 5.5. Nursery flats with 60-70 plants each were supported via a magnetic metal rack in a steel vacuum chamber containing the inoculation fluid. The top ⅔rds of each plant was submerged in the inoculation fluid. A vacuum (−5 in Hg for 30 seconds) was applied to the chamber. The plants were removed from the vacuum chamber and grown in greenhouses for 1-2 weeks prior to planting outside in a commercial field. Chemical analysis was performed on these plants to score the effectiveness of the treatment.

The plants that resulted from these processes were intended to act both as production plants as well as vegetative propagation material for subsequent growth cycles.

Example 5

Disclosed herein is an illustrative example of modularity of enhancement protocol. The previous examples provide methods of how CBGA production can be enhanced in Cannabis plants. The same methodology with a different CRISPR cut site, alternate gene knockout, or knockdown procedure, can result in enhancing any cannabinoid of interest. For example: reducing only CBDA-synthase would result in more THCA and CBCA being produced, likewise reducing only THCA-synthase produces more CBDA and CBCA, and reducing THCA-synthase and CBD-synthase at the same time would boost the levels of CBCA and CBGA that are produced. Finally, by targeting other steps in the synthesis pathway such as the genes that are responsible for the prenylation, cyclization or polyketide synthesis steps; many other cannabinoids can be specified for enhanced production such as THCVA, CBDVA, CBCVA, CBGVA, etc.

The above illustrative examples for CBGA enhancement is used to demonstrate a general method of this that can be applied to enhancing cannabinoid production for other cannabinoids disclosed herein in plants of genus Cannabis.

Example 6

Disclosed herein is an illustrative example of growing plants of genus Cannabis with increased CBD production.

A collection of plants (60,000) targeting enhanced production of CBD was created using the methodology described above in Example 4. The enhanced (i.e., modified) plants of genus Cannabis were grown on a 200-acre hemp farm in the eastern Colorado area, where they were evenly dispersed within a collection of natural, non-enhanced plants (control), with all of the plants exposed to identical growing conditions.

To assess the differences between the enhanced plants and the control plants, cuttings from the plants top shoots were taken at random from 16 enhanced plants, which were evenly dispersed across the hemp farm. The CBD levels were measured for these 16 enhanced plants by extracting the plant cuttings with isopropanol, filtering away the insoluble plant material, and analyzing the extract via analytical SFC.

The results showed that the CBD production in the enhanced plants were approximately doubled vis-a-vis the CBD production in the non-enhanced control plants, whereas the total potency of the enhanced plants remained unchanged.

Example 7

Disclosed herein is an illustrative example of growing plants of genus Cannabis with increased CBG production.

A collection of plants (30,000-40,000) targeting enhanced production of CBG was created using the methodology describe above in Example 4. The enhanced (i.e., modified) plants were grown on a 30-acre hemp farm in the eastern Colorado area, where they were evenly dispersed within a collection of natural, non-enhanced plants (control), with all of the plants exposed to identical growing conditions.

To assess the differences between the enhanced plants and the control plants, cuttings from the plants top shoots were taken at random from 16 enhanced plants, which were evenly dispersed across the hemp farm. The CBG levels were measured for these 16 enhanced plants by extracting the plant cuttings with isopropanol, filtering away the insoluble plant material, and analyzing the extract via analytical SFC.

The results showed that the CBG production in the enhanced plants of genus Cannabis were approximately doubled vis-a-vis the CBG production in the non-enhanced control plants of genus Cannabis, whereas the total potency of the enhanced plants remained unchanged.

Example 8

Disclosed herein is one illustrative example of THCA synthase and CBDA synthase double CRISPR cut via homology for insertion into a vector, called the "Ebbu" vector.

Below is an illustrative example for the design of a sgRNA molecule for cutting both THCA and CBDA synthase coding sequence. A single cut was used based on high levels of homology between the genes. The position was at 452 bp in reverse compliment orientation, at the end of PAM sequence from the start codon based on current working alignment of the THCA and CBDA synthases.

Original grab from aln. for RevComp. (CCN) site

```
                                            (SEQ ID NO: 1)
        GCCGGAGCTA CCCTTGGAGA AGTTTATTAT TGGG
```

Annotation of Above:

```
                                            (SEQ ID NO: 2)
        PAMrc:           CCG; GAGCTACCCTTGGAGAAGTT
                         TATTATTGGG
                                            (SEQ ID NO: 3)
        SumRevC:         CCGGAGCTACCCTTGGAGAAGTT (SEQ ID NO: 4)
        SumInCutOrient:  AACTTCTCCAAGGGTAGCTCCGG
```

Annotation of Correct Orientation: gRNA PAM

```
                                            (SEQ ID NO: 4)
        AACTTCTCCAAGGGTAGCTC CGG
```

The Following Sequence was Added to the CRISPR Cassette:

```
                                            (SEQ ID NO: 5)
            AACTTCTCCAAGGGTAGCTC
```

NCBI BLAST OK/No: Yes, No Other Genes with Homology.

Sequence for Assembly:

```
                                            (SEQ ID NO: 6)
CACAATTCCACACAACATACGAGCCCTTTTTTCTTCTTCTTCGTTCATA

CAGTTTTTTTTGTTTATCAGCTTACATTTTCTTGAACCGTAGCTTTCGT

TTTCTTCTTTTTAACTTTCCATTCGGAGTTTTTGTATCTTGTTTCATAGT

TTGTCCCAGGATTAGAATGATTAGGCATCGAACCTTCAAGAATTTGATTG

AATAAAACATCTTCATTCTTAAGATATGAAGATAATCTTCAAAAGGCCCC

TGGGAATCTGAAAGAAGAAGCAGGCCCATTTATATGGGAAAGAACAAT

AGTATTTCTTATATAGGCCCATTTAAGTTGAAAACAATCTTCAAAAGTCC

CACATCGCTTAGATAAGAAAACGAAGCTGAGTTTATATACAGCTAGAGTC

GAAGTAGTGATTGAACTTCTCCAAGGGTAGCTCGTTTTAGAGCTAGAAAT
```

-continued

AGCAAGTTAAAATAAGGCTAGTCCGTTATCAACTTGAAAAAGTGGCACCG

AGTCGGTGCTTTTTTTCTAGACCCAGCTTTCTTGTACAAAGTTGGCATTA

AGCGGAGAATTAAGGGAGTCACG

Although the present invention herein has been described with reference to various exemplary embodiments, it is to be understood that these embodiments are merely illustrative of the principles and applications of the present invention. Those having skill in the art would recognize that various modifications to the exemplary embodiments may be made, without departing from the scope of the invention.

Moreover, it should be understood that various features and/or characteristics of different embodiments herein may be combined with one another. It is therefore to be understood that numerous modifications may be made to the illustrative embodiments and that other arrangements may be devised without departing from the scope of the invention.

Furthermore, other embodiments of the invention will be apparent to those skilled in the art from consideration of the specification and practice of the invention disclosed herein. It is intended that the specification and examples be considered as exemplary only, with a scope and spirit being indicated by the claims.

Finally, it is noted that, as used in this specification and the appended claims, the singular forms "a," "an," and "the," include plural referents unless expressly and unequivocally limited to one referent, and vice versa. As used herein, the term "include" or "comprising" and its grammatical variants are intended to be non-limiting, such that recitation of an item or items is not to the exclusion of other like items that can be substituted or added to the recited item(s).

What is claimed is:

1. A plant of genus *Cannabis*, comprising:
   a total cannabinoid content;
   a modified genetic material within a genome of the plant of the genus *Cannabis*, wherein the modified genetic material comprises:
   a modified cannabidiolic acid (CBDA) synthase-encoding gene having a cut in the CBDA synthase-coding sequence, wherein the cut inhibits functionality of the CBDA synthase;
   a modified tetrahydrocannabinolic acid (THCA) synthase-encoding gene having a cut in the THCA synthase-coding sequence, wherein the cut inhibits functionality of the THCA synthase;
   and is obtained by SEQ ID NO: 6; and
   an increased cannabigerolic acid (CBGA) content relative to a control plant of the genus *Cannabis* that does not comprise the modified genetic material.

2. A method of producing the plant of genus *Cannabis* of claim 1, the method comprising:
   introducing the nucleotide sequence of SEQ ID NO: 6 into the plant.

3. The method of claim 2, wherein the method comprises introducing an RNA guide.

4. The method of claim 3, wherein the method comprises a CRISPR/Cas9 system.

* * * * *